US008475361B2

(12) United States Patent
Barlow et al.

(10) Patent No.: US 8,475,361 B2
(45) Date of Patent: Jul. 2, 2013

(54) PERCUTANEOUS OR NATURAL-ORIFICE MEDICAL PROCEDURE AND SYSTEM THEREFOR

(75) Inventors: David E Barlow, Coopersburg, PA (US);
Takayasu Mikkaichi, Tokyo (JP);
Kensei Nakahashi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1012 days.

(21) Appl. No.: 11/650,123

(22) Filed: Jan. 5, 2007

(65) Prior Publication Data
US 2007/0255100 A1 Nov. 1, 2007

Related U.S. Application Data

(63) Continuation-in-part of application No. 11/327,788, filed on Jan. 6, 2006, now abandoned.

(60) Provisional application No. 60/759,119, filed on Jan. 13, 2006.

(51) Int. Cl.
*A61B 1/00* (2006.01)
*A61B 1/04* (2006.01)
*A61B 1/06* (2006.01)

(52) U.S. Cl.
USPC ............ 600/113; 600/109; 600/114; 600/160

(58) Field of Classification Search
USPC .................. 600/101, 111, 113, 102, 109, 160
See application file for complete search history.

(56) References Cited

U.S. PATENT DOCUMENTS

| 5,368,015 A |   | 11/1994 | Wilk |          |
|-------------|---|---------|------|----------|
| 5,395,030 A |   | 3/1995  | Kuramoto et al. | |
| 5,458,131 A | * | 10/1995 | Wilk | 600/105 |
| 5,653,677 A | * | 8/1997  | Okada et al. | 600/112 |

(Continued)

FOREIGN PATENT DOCUMENTS

| EP | 1 637 064 A1 | 3/2006 |
| JP | 7-265264     | 10/1995 |
| JP | 07-275195    | 10/1995 |
| JP | 2000-32442   | 1/2000 |

(Continued)

OTHER PUBLICATIONS

Extended Supplementary European Search Report dated Mar. 21, 2011.

*Primary Examiner* — Alireza Nia
(74) *Attorney, Agent, or Firm* — Scully, Scott, Murphy & Presser, P.C.

(57) ABSTRACT

A medical procedure and a system are provided so that two visions are obtainable through natural orifices by means of two observational apparatuses, or one the two visions is selectable. The medical procedure through a natural orifice comprises: forming an orifice in a hollow organ by using a device inserted into the hollow organ from a natural orifice of a patient; introducing a first observation device from said orifice formed in said hollow organ into an abdominal cavity; introducing a second observation device from said orifice formed in said hollow organ into the abdominal cavity; arranging said second observation device in a position different from that of said first observation device; simultaneously or selectively displaying an image obtained from said first observation device and an image obtained from said second observation device; and performing a desired procedure in the abdominal cavity while confirming the images.

5 Claims, 25 Drawing Sheets

U.S. PATENT DOCUMENTS

| | | | |
|---|---|---|---|
| 5,681,260 A | 10/1997 | Ueda et al. | |
| 5,813,976 A * | 9/1998 | Filipi et al. | 600/102 |
| 6,636,254 B1 | 10/2003 | Onishi et al. | |
| 6,689,056 B1 * | 2/2004 | Kilcoyne et al. | 600/300 |
| 6,986,738 B2 * | 1/2006 | Glukhovsky et al. | 600/109 |
| 6,991,602 B2 * | 1/2006 | Nakazawa et al. | 600/101 |
| 7,001,329 B2 * | 2/2006 | Kobayashi et al. | 600/114 |
| 7,122,001 B2 * | 10/2006 | Uchiyama et al. | 600/103 |
| 7,169,104 B2 * | 1/2007 | Ueda et al. | 600/104 |
| 2002/0111534 A1 | 8/2002 | Suzuki et al. | |
| 2004/0175289 A1 * | 9/2004 | Takizawa et al. | 422/20 |
| 2004/0225191 A1 | 11/2004 | Sekine et al. | |
| 2005/0049460 A1 | 3/2005 | Mikkaichi et al. | |
| 2005/0165272 A1 * | 7/2005 | Okada et al. | 600/114 |

FOREIGN PATENT DOCUMENTS

| | | |
|---|---|---|
| JP | 2000-166936 | 6/2000 |
| JP | 2003-93332 | 4/2003 |
| JP | 2003-111763 | 4/2003 |
| JP | 2003-135388 | 5/2003 |
| JP | 2003-220023 | 8/2003 |
| JP | 2004-267772 | 9/2004 |
| JP | 2005-204806 | 8/2005 |
| WO | WO 2004/071284 A1 | 8/2004 |
| WO | WO 2004/112593 A1 | 12/2004 |
| WO | 2005/009227 A1 | 2/2005 |
| WO | 2006/113108 A2 | 10/2006 |

* cited by examiner

PERCUTANEOUS OR NATURAL-ORIFICE MEDICAL PROCEDURE AND SYSTEM THEREFOR

CROSS-REFERENCE TO RELATED APPLICATION

The present application claims priority on U.S. patent application Ser. No. 11/327,788 filed Jan. 6, 2006, and U.S. provisional application No. 60/759,119, filed Jan. 13, 2006, the contents of which are incorporated herein by reference.

BACKGROUND OF THE INVENTION

1. Field of the Invention

The present invention relates to a medical procedure or action performed through a natural orifice of a living body. This invention comprises a new technique to hold an imaging capsule in the patient's lumen of abdominal cavity by means of a percutaneous manipulator placed through the abdominal wall.

2. Description of the Related Art

In the case where a medical procedure (including observation, treatment, and the like, which is the same hereunder) is performed for a human organ and the like, there is known a laparoscopic operation for manipulating by opening a plurality of orifices in the abdominal wall, instead of largely incising the abdominal wall, and inserting a laparoscope, a forceps, and a scalpel into the respective orifices. The laparoscopic operation can be completed simply by opening small orifices in the abdomen, having an advantage of quick recovery of the patient.

However, recently, as a method of further reducing the burden on a patient, there is proposed a manipulation (or manipulation) performed by inserting a flexible endoscope from a natural orifice such as the mouth, a nostril, and the anus. An example of such a medical procedure is disclosed in U.S. Pat. No. 5,458,131. A flexible endoscope is inserted from the mouth of a patient, and the endoscope is sent out from an orifice formed in the stomach wall into the abdominal cavity. The observation of the abdominal cavity is performed by an observation device provided at the distal end of the endoscope. Furthermore, an organ is treated by using a treatment tool passed through the endoscope, and a treatment tool inserted from another orifice opened in the stomach, or inserted from the anus through an orifice opened in the lower gastrointestinal tract, into the abdominal cavity. After the manipulation in the abdominal cavity is completed, the endoscope and treatment tool(s) are withdrawn, and the orifices are closed. Upon closure of an orifice, the tissue around the orifice is drawn together, and the tissue is bound up with an O-ring so as to close the orifice.

It is an object of the present invention to provide a medical procedure and a system where two visions are obtainable through natural orifices by means of two observational apparatuses, or one the two visions is selectable.

Video imaging capsules are commonly used to view the interior of the GI tract, particularly the lumen of the small intestine. The imaging capsule is swallowed by the patient and carried by peristalsis through the stomach and intestines, collecting and transmitting images of the patient's GI tract to an external recorder.

It is now common to image the abdominal cavity by means of a laparoscope, a tubular optical instrument placed into the abdominal cavity through a stab incision in the patient's abdominal wall. Typically the laparoscope is inserted into a lumen of the abdominal cavity via a trocar, a hollow tubular instrument designed to create a passageway through the abdominal wall for the introduction of laparoscopes, probes and therapeutic devices, and often incorporating a means to inject or hold gas within the abdominal cavity for insufflation.

Another object of the present invention is to replace the viewing function of the laparoscope with a self-contained imaging capsule which is held in place by a percutaneous manipulator. Another object of the present invention to provide a percutaneous manipulator having a means for controlling the direction of capsule maintained in the lumen of the abdominal cavity.

SUMMARY OF THE INVENTION

The present invention directed to a natural-orifice medical procedure and system in which two visions are obtainable, or one the two visions is selectable, comprises: forming an opening in a hollow organ by using a device inserted into the hollow organ from a natural orifice of a patient; introducing a first observation device from the opening formed in the hollow organ into an abdominal cavity; introducing a second observation device from the opening formed in the hollow organ into the abdominal cavity; arranging the second observation device in a position different from that of the first observation device; simultaneously or selectively displaying an image obtained from the first observation device and an image obtained from the second observation device; and performing an intended manipulation in the abdominal cavity while confirming the images.

DETAILED DESCRIPTION OF THE INVENTION

Embodiments will be hereafter explained in detail. In the following description, the same reference symbols are used for the same components, and duplicate description is omitted.

First Embodiment

Figure 1:
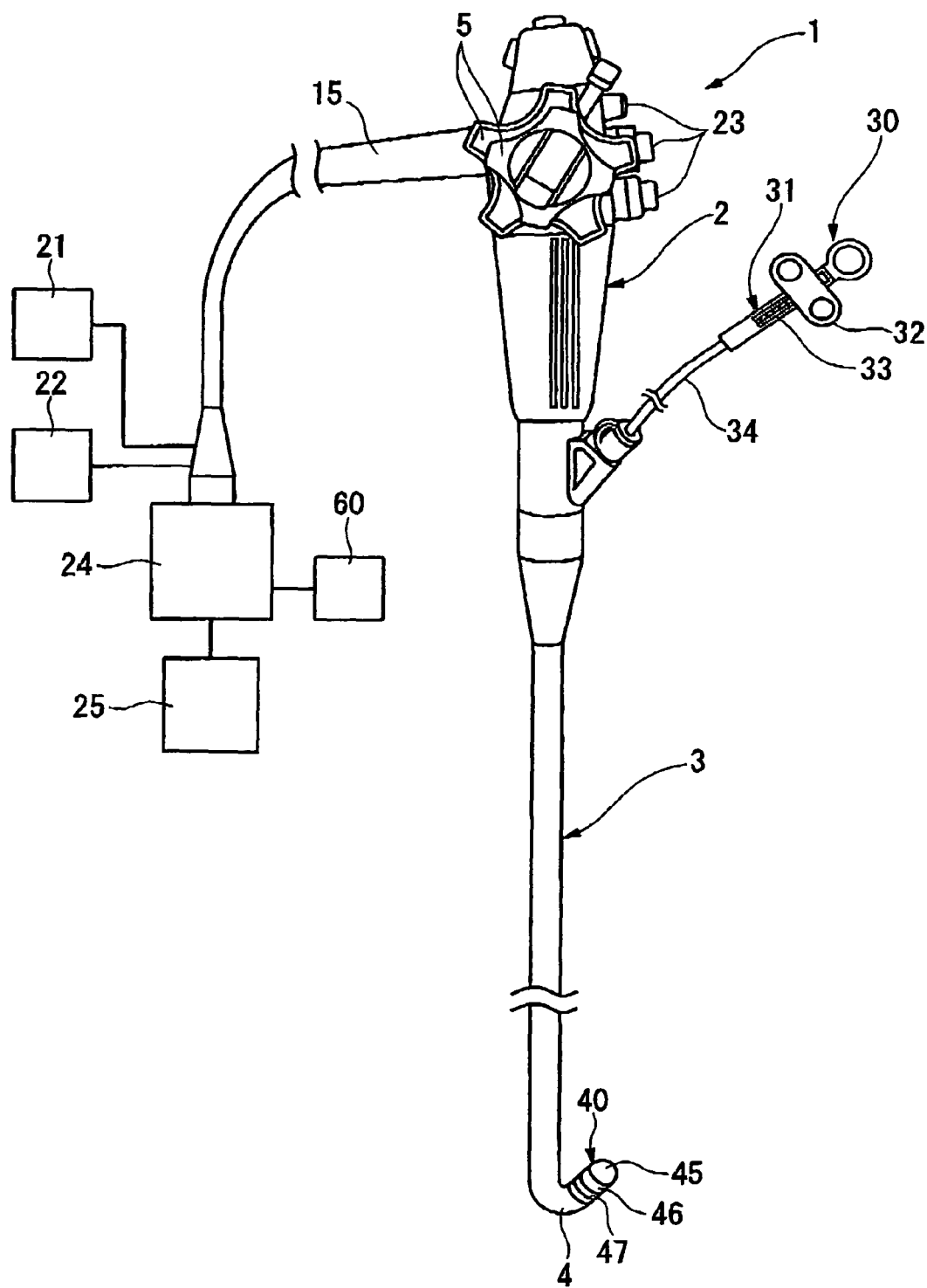
FIG. 1 is a view showing an endoscope as an example of a device used for performing a medical procedure in an embodiment, holding a capsule endoscope as a second observation device.
Figure 2:
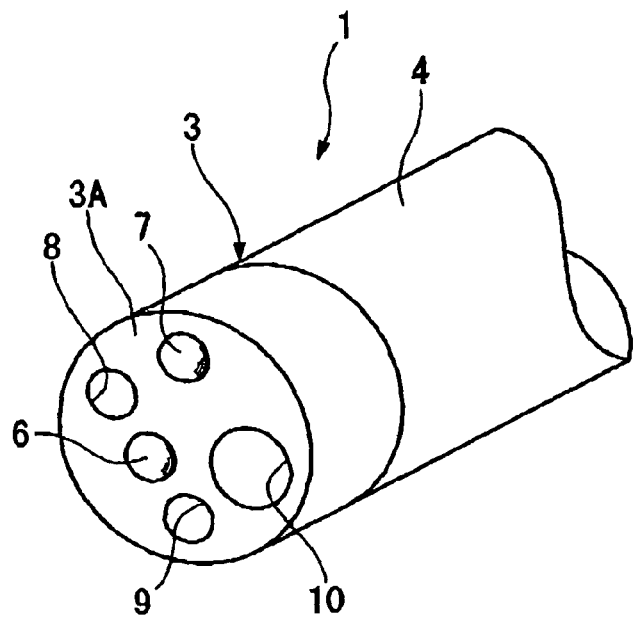
FIG. 2 is a perspective view of the distal end of the endoscope, showing a first observation device.

FIG. 1 shows a flexible endoscope (hereunder, called an endoscope) serving as a device used in the present embodiment, holding a capsule endoscope at the distal end of an insertion portion thereof. The endoscope 1 has an extending insertion portion 3 which is to be inserted into a patient's body from an operation portion 2 operated by an operator. The insertion portion 3 is slender and flexible. A distal end 4 of the insertion portion 3 can be curved by angle knobs 5 of the operation portion 2. As shown in FIG. 2, an illuminating device 7 and a first observation device 6 for observing inside the body are disposed on a distal face 3A of the insertion portion 3. The first observation device 6 comprises, for example, an observational optical system such as an object lens, and a CCD (Charged Coupled Device) as an imager. The illuminating device 7 is configured to guide light illuminated from a light source unit outside of the body, by means of an optical fiber. In this configuration, an output signal from the imager may be transmitted to a controller 24 described later through a signal wire passed through the insertion portion 3. Moreover, in this configuration, an output signal from the imager may be transmitted to the controller 24 by wireless means. Furthermore, the illuminating device 7 may comprise a publicly known light emission element (for example, light emitting diode) or the like.

Moreover, distal orifices corresponding to various channels 8 to 10 are disposed on the distal face 3A of the insertion portion 3. A fluid supply channel 8 is a duct used for supplying a fluid into the body. A suction channel 9 is a duct used for sucking a fluid from the body. Treatment tools are disposed through a work channel 10. The respective channels 8 to 10 are extended from the insertion portion 3 toward the operation portion 2. However, the endoscope 1 is not limited to this configuration. For example, in this configuration, the work channel 10 may be used for suction work instead of omitting the suction channel 9. Moreover, a plurality of work channels 10 may be provided.

The proximal orifice of the work channel 10 is also provided on a side of the operation portion 2. The other channels 8 and 9 are connected to a fluid supply device 21 and a suction device 22 through a universal cable 15 shown in FIG. 1. Operation button 23 disposed on the operation portion 2 permits supplying or sucking air and liquid. The endoscope 1 is also connected to the controller 24, through the universal cable. The controller 24 for controlling the endoscope 1 is installed with an image processor and a light source, thus the controller 24 is capable of outputting various images (images) to a monitor 25.

Figure 3:
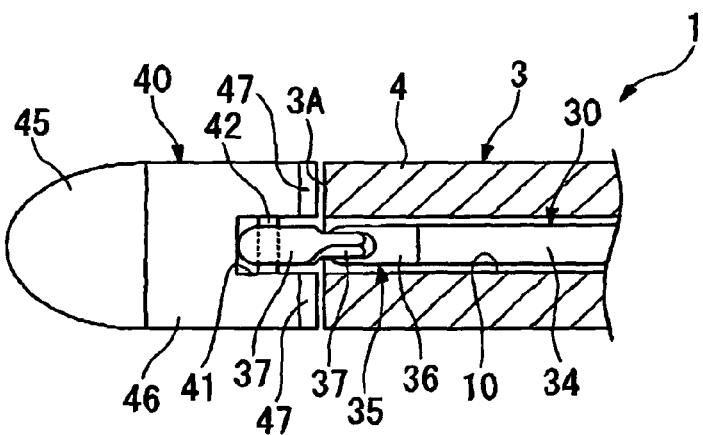
FIG. 3 illustrates is a holding state of the capsule endoscope in a partial cross-sectional view.
Figure 4:
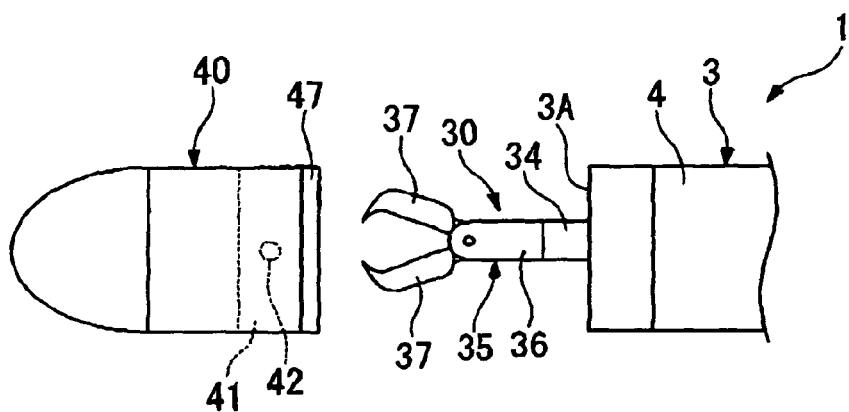
FIG. 4 is a view showing a process for holding the capsule endoscope.

FIG. 1 shows a grasping forceps 30 as an example of a treatment tool passed through the work channel 10 of the endoscope 1. The grasping forceps 30 has a forceps operation portion 31 having a handle 32 movable in a back-and-forth based on the operator's operation. A wire 33 is fixed to the handle 32. The wire 33 is led into a flexible forceps insertion portion 34 extending to the distal end of the forceps operation portion 31. As shown in FIG. 3, this forceps insertion portion 34 is passed through the work channel 10. A treatment portion 35 is provided to the distal end of the forceps insertion portion 34. As shown in FIGS. 3 and 4, the treatment portion 35 is configured to support a pair of forceps members 37 on a supporting portion 36 so as to freely open. The pair of forceps members 37 is connected to the wire 33, and can be opened and closed according to a back-and-forth movement of the handle 32.

The treatment portion 35 of the grasping forceps 30 in this configuration holds a capsule endoscope 40 as a second observation device in the present embodiment. The capsule endoscope 40 has an outline of a cylindrical shape with a spherical distal end. The proximal face is provided with a radially extending groove 41 in a concave manner. Fixed to the groove 41 is a pin 42 configured to transverse the groove 41. Holding this pin 42 by the forceps members 37 serving as a holding part of the grasping forceps 30 provides a support to the capsule endoscope 40 by means of the grasping forceps 30. The width and the depth of the groove 41 are in a size which allows insertion and withdrawal of the treatment portion 35. As shown in FIG. 1 and FIG. 3, the capsule endoscope 40 is abutted against the distal face 3A of the insertion portion 3. The outer diameter thereof is not greater than the outer diameter of the distal end 4 of the insertion portion 3 so as not to interfere with insertion into the body.

As shown in FIG. 1 and FIG. 3, the capsule endoscope 40 has an approximately hemispherical transparent hood 45 on the distal end. Furthermore, it has a capsule type casing 46 having a flat proximal end except for the groove 41. A pair of semicircular magnetic bodies 47 is fixed to the proximal end of the casing 46 so as to avoid the groove 41. The magnetic body 47 may be a hard magnetic body material which generates a magnetic force by itself, or a soft magnetic body which is magnetized when exposed to a magnetic field.

Figure 5:
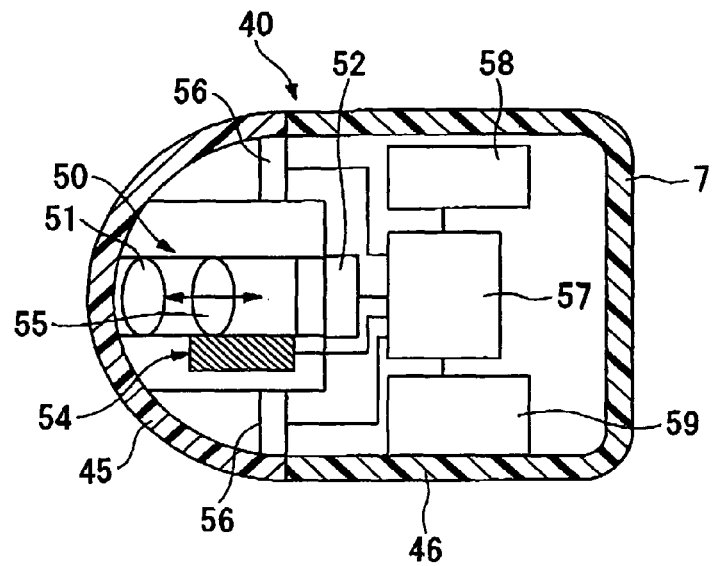
FIG. 5 is a cross-sectional view showing the construction of the capsule endoscope.

As shown in FIG. 5, disposed in the casing 46 toward the transparent hood 45 is a second observation portion 50 serving as an observational optical device. The second observation portion 50 has an object lens 51 and an imager 52 arranged in the imaging position of the object lens 51, and is constructed so that the magnification can be changed by moving a zoom lens 55 by means of a zoom mechanism 54. The second observation portion 50 preferably comprises the zoom mechanism 54, however the zoom mechanism 54 is a dispensable component in the present embodiment. Disposed around the second observation portion 50 is an illumination part 56 for illuminating the view field of the second observation portion 50. For the illumination part 56, for example a plurality of LEDs (Light Emitting Diodes) are used. The second observation portion 50 and the illumination part 56 are connected to a control circuit 57. Provided to the control circuit 57 ARE a camera control unit (CCU) connected to the imager 52, a circuit which turns on the illumination part 56, and so forth. Connected furthermore to the control circuit 57 are an antenna 58 and a battery 59.

The capsule endoscope 40 obtains an observation image (endoscopic image) under light of the illumination part 56. The observation image is converted into electric signals and output to the control circuit 57 by the imager 52. The control circuit 57 sends the electric signals of the observation image to the antenna 58 and oscillates transmits them toward outside of the body as radio signals. The receiver 60 shown in FIG. 1 receives these radio signals and outputs to the controller 24 of the endoscope. That is, an image of the capsule endoscope 40 (hereunder, called a second observation image) can be displayed on a monitor 25 via the receiver 60. Detailed description of the capsule endoscope is disclosed in International Patent Application Publication No. WO2004/112593. The contents disclosed in the International Patent Application WO2004/112593 are incorporated in the present embodiment.

The operation of the present embodiment will be described. Described hereunder is a manipulation for treating an organ or a tissue (hereunder, called a target site) serving as an object on which a desired medical procedure is performed, by inserting the endoscope 1 from a patient's mouth as a natural orifice of a living body. However, the natural orifice subject to the insertion of the endoscope 1 is not limited to the mouth, and may be a nostril or the anus. Moreover, treatments as a medical procedure are applicable to various actions such as suture, observation, incision, and cell sampling.

Figure 6:
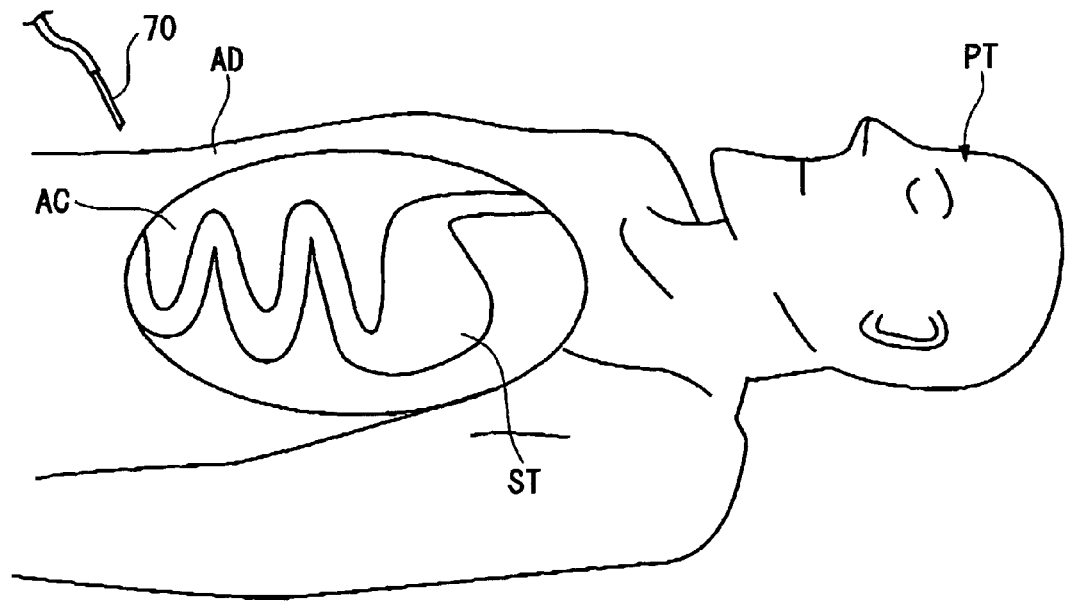
FIG. 6 illustrates a patient laid on his back to be subject to a manipulation in an explanatory diagram.

As shown in FIG. 6, a patient PT is laid on his back so that the abdomen AD is uppermost. Then a pneumoperitoneal needle 70 is pierced into the abdomen AD, and carbon dioxide gas or the like is sent into the abdominal cavity AC to expand the abdominal cavity. It is desirable to expand the abdominal cavity in order to ensure a space for performing a medical procedure in the abdominal cavity, however a pneumoperitoneum is not necessarily performed as long as a desired space can be ensured. Moreover, a method of expanding the abdominal cavity is not limited to a method of expanding by a gas, and may be a publicly known lifting method so as to keep a space in the abdominal cavity. Moreover, the timing to expand the abdominal cavity may be after a device (for example, the endoscope 1) is introduced into the abdominal cavity.

Figure 7:
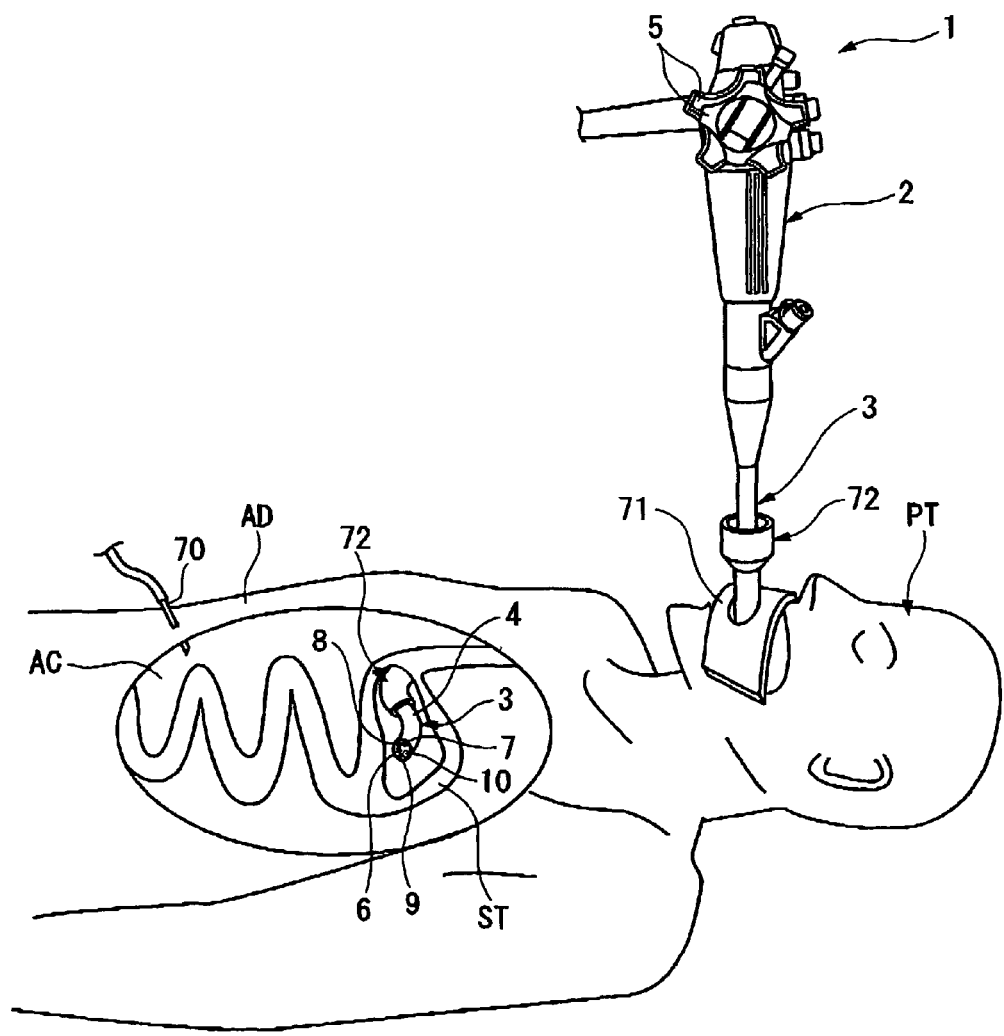
FIG. 7 is a view showing the endoscope inserted into the stomach.

As shown in FIG. 7, after the abdomen AD of the patient PT is expanded by means of pneumoperitoneum, the endoscope 1 is passed through from a mouthpiece 71 attached to the patient PT's mouth into the body. Preferably, as shown in FIG. 7, upon insertion of the endoscope 1 into the body, an overtube 72 is used in common. The overtube 72 used as a guide tube for inserting/withdrawing a device having an insertion portion such as the endoscope 1, into/from the body may not be used. Instead of that, the device may be inserted into the body.

The endoscope 1 at this time is not attached with the capsule endoscope 40. After the insertion portion 3 is inserted into the stomach ST, the fluid supply channel 8 is used to send a gas into the stomach ST so as to expand the stomach ST. A device for incision, for example a high frequency knife, is passed through the work channel 10, and the stomach wall is incised. The incision site is desirably an anterior wall of the stomach.

After the stomach wall is incised, the endoscope 1 is withdrawn from the body, and then the grasping forceps 30 are passed through the work channel 10. After projecting the treatment portion 35 from the distal face 3A of the insertion portion 3, the back-and-forth movement of the handle 32 of the forceps operation portion 31 provides the open-and-close movement of the pair of forceps members 37, thereby holding the capsule endoscope 40. As shown in FIG. 3, the backward movement of the grasping forceps 30 projects the magnetic bodies 47 disposed on the proximal end of the capsule endoscope 40 to abut against the distal face 3A of the insertion portion 3.

Figure 8:
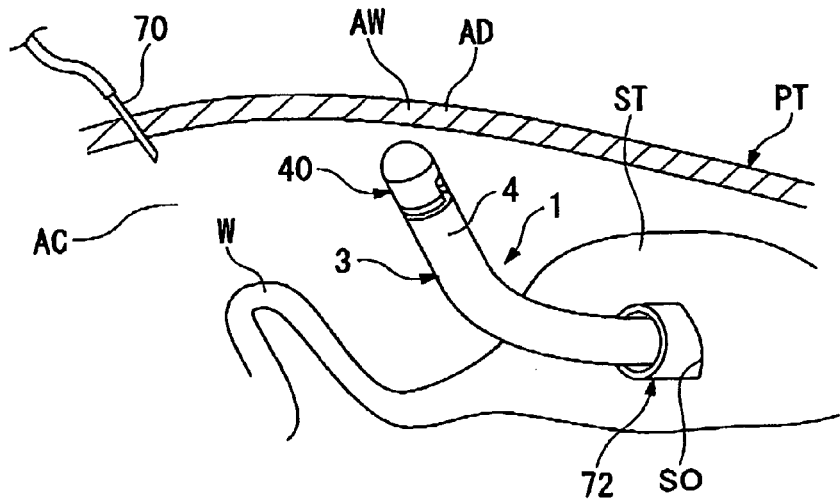
FIG. 8 is a view showing the endoscope introduced from an opening formed in the stomach into the abdominal cavity.

The endoscope 1 is inserted from the patient PT's mouth into the stomach ST while the capsule endoscope 40 is held. For the image of inside the body, an image captured by the second observation portion 50 of the capsule endoscope 40 is used. Moreover, as shown in FIG. 8, the insertion portion 3 is introduced from an opening SO formed by incising the stomach wall, into the abdominal cavity AC. Desirably, the state of target site W should be confirmed by the capsule endoscope 40.

Figure 9:
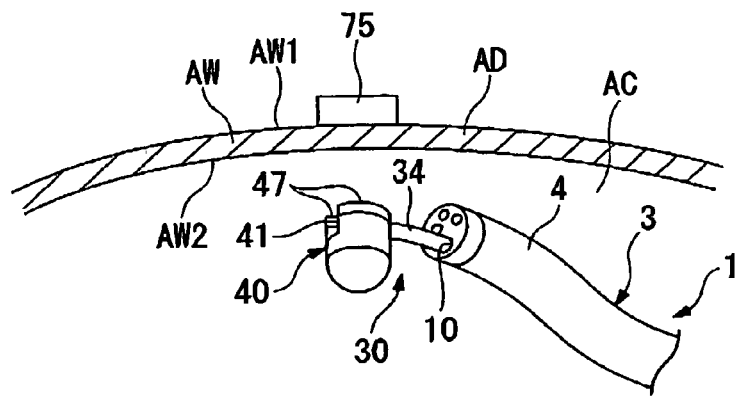
FIG. 9 is a view showing the capsule endoscope that is projected.

The insertion portion 3 is next curved toward the abdominal wall AW. Moving the grasping forceps 30 in the vicinity of the abdominal wall AW separates the capsule endoscope 40 from the endoscope 1. As shown in FIG. 9, the capsule endoscope 40 is rotated about the pin 42 (refer to FIG. 3) with respect to the grasping forceps 30, and hung from the grasping forceps 30. As a result, the magnetic bodies 47 are directed toward the abdominal wall AW. In the present embodiment, the magnetic bodies 47 are provided on the proximal end of the capsule endoscope 40 (the opposite side to the view field direction of the second observation portion 50). Moreover, the direction of the magnetic bodies 47 configured toward the abdominal wall AW is not limited to this configuration. In this configuration, for example, a magnetic body may be arranged in an optional position of the capsule endoscope 40, such as a side of the capsule endoscope 40, and a magnetic force is generated between this magnetic body and a magnetic body set outside of the body, so as to obtain an image of the abdominal cavity at a desired angle.

A magnet 75 is put on an outer surface AW1 (also called the abdomen or the abdomen outer surface) of the abdominal wall AW. While confirming that the target site W can be observed by the capsule endoscope 40 on the display of the monitor 25, the magnetic bodies 47 of the capsule endoscope 40 are attracted to the magnet 75 having the abdominal wall AW therebetween. The magnet 75 is used for placing the capsule endoscope 40 on the abdominal wall AW using the magnetic force effect. In the present embodiment, a permanent magnet is used as the magnet 75, however an electromagnet may be used.

Figure 10:
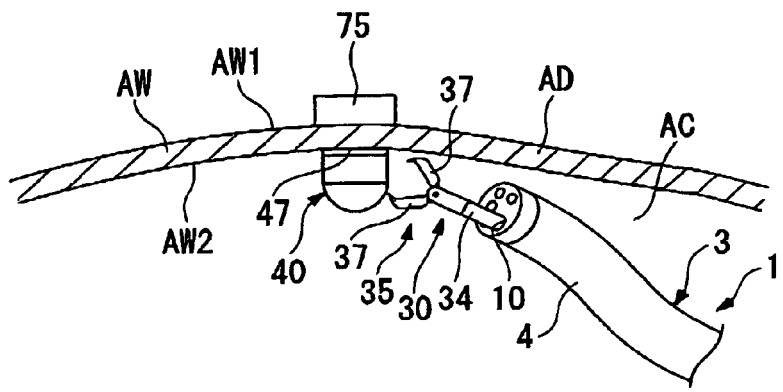
FIG. 10 is a view showing the capsule endoscope attached to a magnet disposed outside of the abdominal wall.

As shown in FIG. 10, this attaches the capsule endoscope 40 to the inner surface AW2 of the abdominal wall AW, and does not drop even if the grasping forceps 30 is opened. The magnet 75 may be previously put in the vicinity of the target site W of the abdominal wall AW, or may be disposed while the position of the capsule endoscope 40 is being searched.

Figure 11:
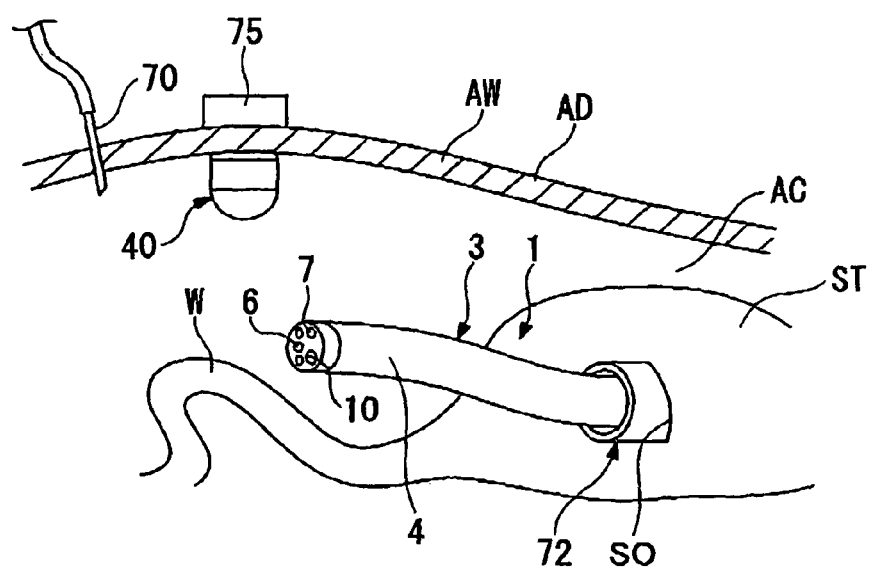
FIG. 11 illustrates how a target site is confirmed by the capsule endoscope and the first observation device of the endoscope.

After the grasping forceps 30 is detached from the capsule endoscope 40, the insertion portion 3 is curved again. As shown in FIG. 11, while searching for the target site W based on images of the first observation device 6 provided on the insertion portion 3, and the capsule endoscope as the second observation device, the endoscope 1 is moved forward to the target site W. The image of the first observation device 6 is a localized image, whereas the image of the capsule endoscope 40 is an image of a wide area where the distal end 4 of the insertion portion 3 enters, that is, an overhead view of the target site W. Therefore, by watching these two images, the position of the insertion portion 3 and the position of the target site W can be ascertained.

Figure 12:
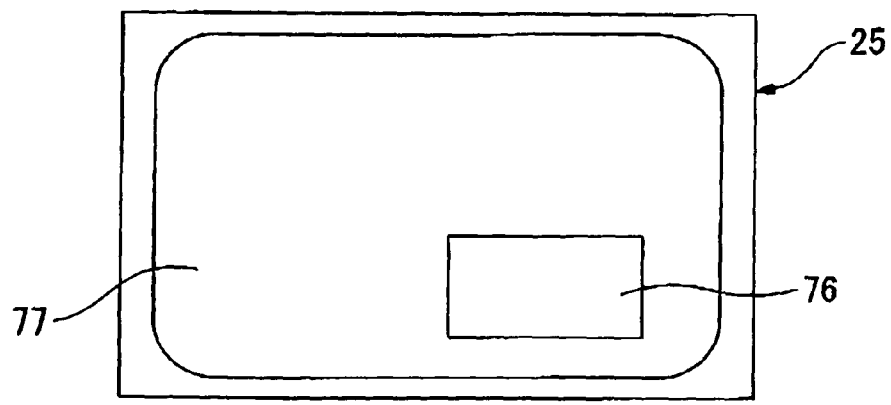
FIG. 12 is an example of an image of the first observation device superposed in an image of the capsule endoscope.

As shown as an example in FIG. 12, image-processing for superimposing an image 77 of the capsule endoscope 40 into an image 76 of the first observation device 6 in the monitor 25 permits the operator merely to confirm the image on one monitor 25. The monitor 25 shows the image 76 of the capsule endoscope 40 in a part of the image 77 of the first observation device 6 of the endoscope 1, and the overall image can be readily ascertained by confirming these two images. These images 76 and 77 can be switched by operating the buttons 23 of the endoscope 1. Instead of displaying the partial superimposed image, these two images 76 and 77 may be displayed separately on the screen. Moreover, the images 76 and 77 may be separately displayed in two monitors. Furthermore, informative image as the second observation image may be obtained by manipulating the magnet 75 outside of the body to move the position and the view field direction of the capsule endoscope 40 as the second observation device while a medical procedure is performed in the abdominal cavity AC.

Figure 13:
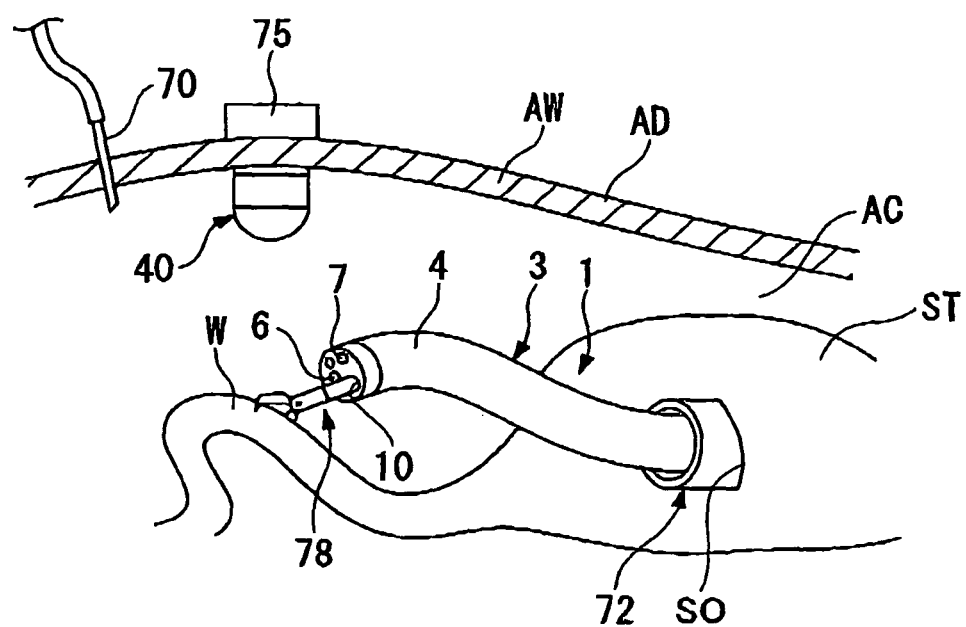
FIG. 13 is an explanatory diagram illustrating how a manipulation for treating a treatment target site is conducted by a forceps passed through a work channel.

After the insertion portion 3 is faced to the target site W, the grasping forceps 30 is withdrawn, and a treatment tool is passed through the work channel 10 instead. For example, in the case of FIG. 13, a tissue of the target site W is resected by using a resection forceps 78 while watching the image of the first observation device 6 and the image of the capsule endoscope 40 as the second observation device. Magnifying the size of the image 76 of the first observation device 6 provides magnified image of the target site W and the resection forceps 78, thereby facilitating the operator's operation. The construction may be such that the size of the image 77 of the first observation device 6 and the size of the second image 76 (second observation image) of the second observation portion 50 of the capsule endoscope 40 can be selectively switched according to the operation of the operator. For example, the construction may be such that when the device is made to approach the target site, the image 77 of the first observation device is displayed on a part of the second image 76 of the second observation device, and then when a medical procedure is performed, the image processing is switched so that the second image 77 of the second observation portion 50 is displayed on a part of the image 77 of the first observation device 6.

If the treatment of the target site W is incision of a tissue for example, then after the tissue is incised, a treatment tool for suture is passed through the endoscope 1 and the incised orifice is sutured. After that, the grasping forceps 30 is passed through the endoscope 1 again, and the capsule endoscope 40 is collected.

Figure 14:
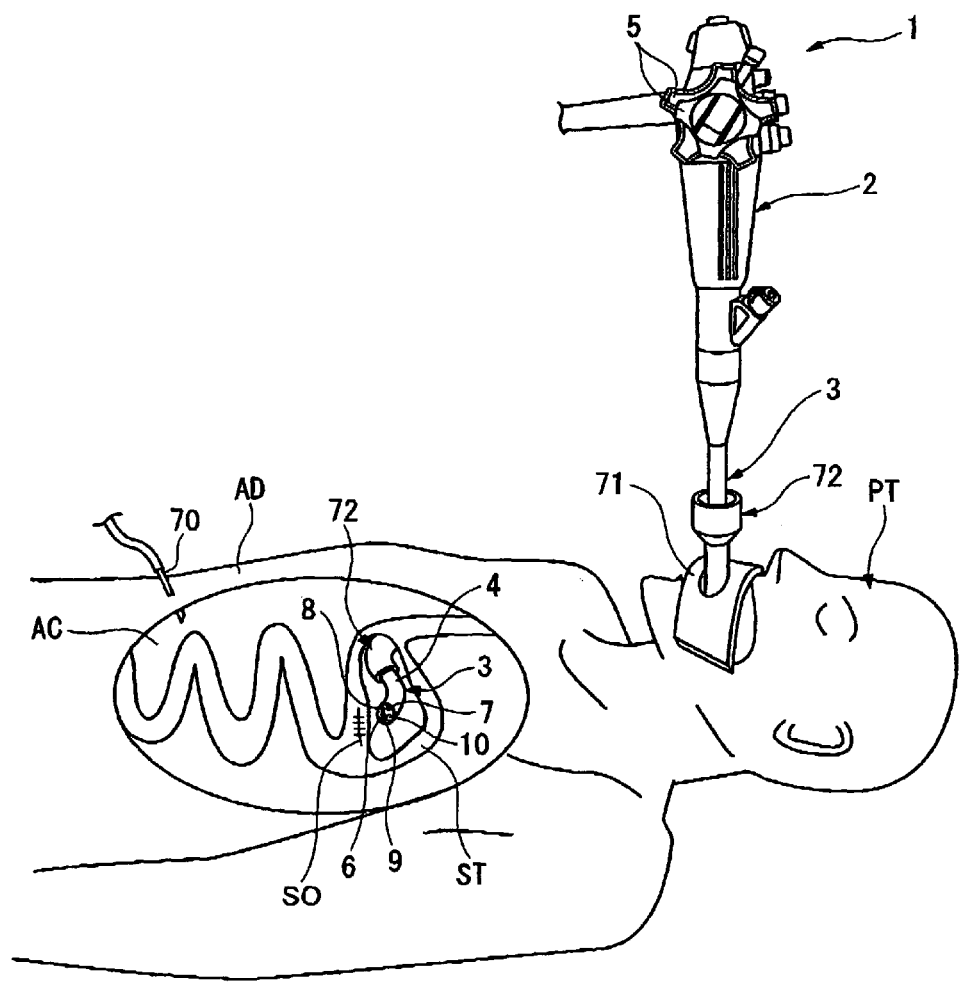
FIG. 14 is a view showing the opening sutured after the endoscope and the capsule endoscope are brought back into the stomach.

To be more specific, the treatment portion 35 of the grasping forceps 30 is inserted into the groove 41 in the capsule endoscope 40, and the pin 42 is hold between the pair of forceps members 37 which freely opens and closes. After the holding of the capsule endoscope 40 is confirmed by the first observation device 6, the magnet 75 outside of the body is removed. Since the capsule endoscope 40 comes off from the inner surface AW2 of the abdominal wall AW and is hung from the grasping forceps 30, if the grasping forceps 30 is moved backward, the magnetic bodies 47 of the capsule endoscope 40 are abutted against the distal face 3A of the insertion portion 3. The endoscope 1 is brought back into the stomach ST from the orifice SO in the stomach wall and withdrawn from the patient PT's mouth in this state, and then the capsule endoscope 40 is taken out to outside of the body. Furthermore, inserting the endoscope 1 through which the treatment tool for suture passed therethrough is inserted from the mouth again, and the orifice SO in the stomach wall is sutured. As shown in FIG. 14, after the suture of the orifice SO is completed, the endoscope 1 is withdrawn from the patient, and the pressure on the abdominal cavity AC is removed, after which the pneumoperitoneal needle 70 is withdrawn, and the manipulation is completed. The timing when the capsule endoscope 40 serving as the second observation device will be taken out from the body, is set before suture, however it may be brought back into the stomach ST before the suture, and taken out from the stomach ST after the suture.

According to the present embodiment, when a manipulation is performed by introducing the endoscope 1 from the mouth through the stomach ST into the abdominal cavity AC, the capsule endoscope 40 that can be used apart from the endoscope 1 is arranged as the second observation device on the inner surface AW2 of the abdominal wall AW. Therefore, an image in a wide view field can be obtained. Since images including the target site W and the insertion portion 3 from different angles can be obtained, the operator can readily ascertain the positional relation, the direction, and the movement of respective sites, thus facilitating the manipulation. Particularly when it is difficult to identify the target site W in the view field of the first observation device 6, in a conventional method and device construction, the endoscope 1 has been operated to move the first observation device 6 to change the angle and the view field so as to identify the target site W, thus loading a burden onto the operator and the patient. However, the present embodiment can solve such a problem.

When the abdomen AD of the patient PT is faced upwards, the capsule endoscope 40 is arranged on the inner surface AW2 of the abdominal wall AW. Therefore, the image of the capsule endoscope 40 becomes an image as if the operator overlooks the insertion portion 3, the treatment tool, and the target site W. Furthermore, the manipulation is further facilitated by adjusting the direction of the capsule endoscope 40 or performing image processing so that the vertical, sideways, and lengthwise directions recognized by the operator are matched with the actual directions.

The capsule endoscope 40 arranged on the inner surface AW2 of the abdominal wall AW by using the magnetic bodies 47 does not provide pain to a patient. Since the capsule endoscope 40 can be arranged and detached by simply putting on/taking off the magnet 75 outside of the body, the operation is facilitated. In particular, complicated operations become unnecessary on the inner surface AW2 side of the abdominal cavity AD.

The magnet 75 may be an electromagnet. The capsule endoscope 40 may have a sucker instead of the magnetic bodies 47. By attaching it onto the inner surface AW2 of the abdominal wall AW by means of a sucker, a similar effect to the above can be obtained. Moreover, a recess may be provided in the outer periphery of the proximal end of the capsule endoscope 40 so as to attach a clip to clamp the inner surface AW2 of the abdominal wall AW to the recess. The clip enables the capsule endoscope 40 to be fixed to the abdominal wall AW, and a similar effect to the above can be obtained. The clip is passed through the work channel as a treatment tool. Moreover, the clip may be previously and integrally attached onto the outer periphery of the capsule endoscope 40.

Second Embodiment

A second embodiment is described in detail with reference to the drawings.

Figure 15:
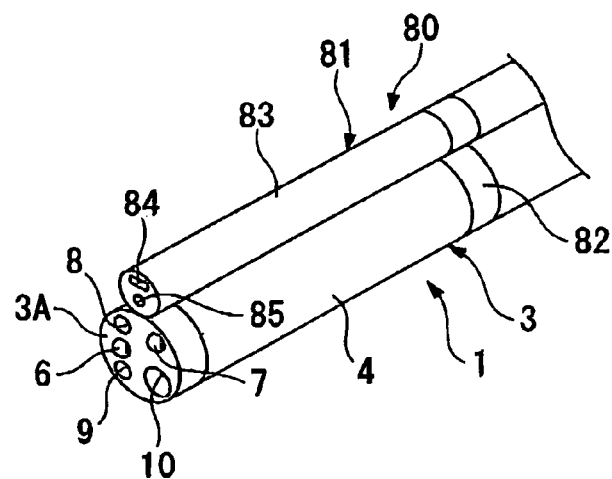
FIG. 15 is a view showing the endoscope attached with a compact scope having a second observation device.

As shown in FIG. 15, the insertion portion 3 of the endoscope 1 is fixed with a small scope 80 as a second observation device in the present embodiment, by a connection member 82. The small scope 80 is an endoscope exclusively for observation, having an illuminating device 84 and a second observation device 85 on the distal end of a flexible insertion portion 81, but not having various channels so as to decrease the diameter. The insertion portion 81 is extended along the insertion portion 3 and is connected by the connection member 82. The distal side from the part connected by the connection member 82 becomes a curvable portion 83. That is, the position where the insertion portion 81 is fixed to the insertion portion 3 is the proximal side from the curvable portion 83, being a position not interfering with curving operations of the respective curvable portions 4 and 83. The curving operation is performed by an operation portion on the hand side. The diameter of the insertion portion 81 is sufficiently narrow compared to the diameter of the insertion portion 3, being a size not interfering with insertion/withdrawal of the endoscope 1. The illuminating device 84 and the second observation device 85 of the small scope 80 have, for example similar constructions to those of the illuminating device 7 and the first observation device 6 of the endoscope 1, and are connected to the controller 24 through the inside of the small scope 80.

The operation of the present embodiment will be described.

Figure 16:
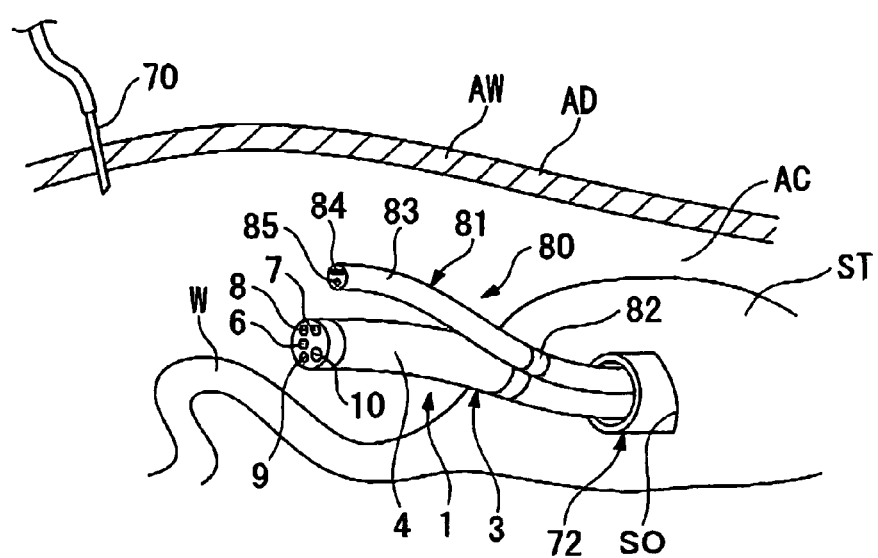
FIG. 16 is a view showing the compact scope curved in the abdominal cavity.

The endoscope 1 attached with the small scope 80 is inserted from the patient PT's mouth into the stomach ST. A high frequency knife is passed through the work channel 10 of the endoscope 1, and the stomach wall is incised to form the opening SO. The endoscope 1 is introduced from the opening SO into the abdominal cavity AC, and the target site W is confirmed by using the first observation device 6 and the second observation device 85. As shown in FIG. 16, moving the second observation device 85 a direction away from the first observation device 6 by curving the curvable portion 83 of the small scope 80 provides two images obtained from different viewpoints.

The operator disposes the insertion portion 3 toward the target site while confirming these two images. The forceps is passed through the work channel 10 of the endoscope 1, and the target site W is treated while confirming the two images. The two images obtained by the first observation device 6 and the second observation device 85 may be displayed either simultaneously or selectively. After the treatment in the abdominal cavity AC is completed, the curvable portion 83 of the small scope 80 is brought back along the insertion portion 3, and then the insertion portion 3 is withdrawn from the abdominal cavity AC back into the stomach. The treatment tool for suture is passed through the work channel 10, and the opening SO in the stomach wall is sutured, and then the endoscope 1 is withdrawn from the body.

According to the present embodiment, when a manipulation is performed by introducing the endoscope 1 from the mouth through the stomach ST into the abdominal cavity AC, the small scope 80 along the insertion portion 3 is used, enabling to arrange the second observation device 85 away from the first observation device 6 at a predetermined distance. Since two images from different angles can be obtained, the operator can readily ascertain the positional relation, the direction, and the movement of respective sites, further facilitating the manipulation. If the construction is such that the second observation device 85 is arranged in a position back from the first observation device 6, or that a wide-angle lens is attached to the second observation device 85, so as to enable to observe a wider view field than that of the first observation device 6, then an image from a wide view field can be obtained as a second observation image, further facilitating the manipulation in this case too.

Similarly to the first embodiment, when a medical procedure is performed in the abdominal cavity AC, a curving operation of the curvable portion 83 of the small scope 80 and/or back-and-forth moving operation of the small scope 80 may be performed so as to move the position of second observation device 85 to a desired location (to change the viewpoint of the second observation device 85).

Since the second observation device 85 is not completely separate from the endoscope 1, the recovery operation can be omitted. Moreover, the position of the second observation device 85 can be readily changed in the middle of manipulation, enabling to obtain optimum images according to the type of manipulation and its progress.

Third Embodiment

A third embodiment is described in detail with reference to the drawings. The present embodiment is characterized in using an overtube (also called a guide tube or a device) for passing an endoscope therethrough.

Figure 17:
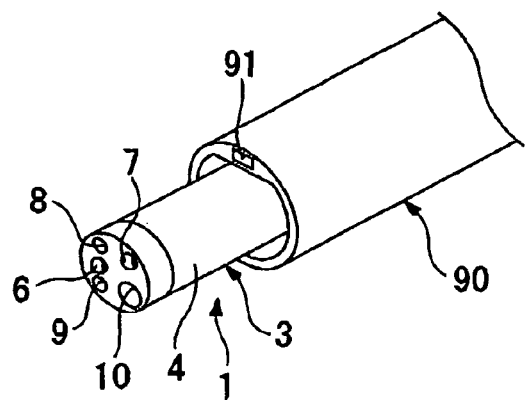
FIG. 17 is a view showing the second observation device provided on the distal end of an overtube.

As shown in FIG. 17, an overtube 90 is made from a flexible and slender barrel, inside of which the endoscope 1 can be inserted in a back-and-forth movable manner. Provided to the distal end of the overtube 90 is a second observation device 91 having an image-capturing face facing forward. This second observation device 91 captures an image in a range illuminated by the illuminating device 7 on the endoscope 1 side, however another illuminating device may be arranged around the second observation device 91.

When a manipulation is performed, the endoscope 1 is guided into the abdominal cavity AC together with the overtube 90, and the target site W is confirmed by respective images of the first observation device 6 and the second observation device 91. After the distal end of the endoscope 1 is pushed out from the overtube 90, the manipulation is performed. The first observation device 6 provided on the endoscope 1 obtains an image from a position close to the treatment tool and the target site W. Since the second observation device 91 provided on the overtube 90 is in a position away from the first observation device 6, it obtains an image of a wide view field including the distal end of the endoscope 1, the treatment tool, and the target site W. The operator performs the procedure while simultaneously or selectively confirming two images in different image-capturing positions.

In the present embodiment, since the manipulation can be performed using two images captured from different points in the insertion direction of the endoscope 1, the positional relation between the target site W and the treatment tool are readily confirmed, facilitating the manipulation. Since the second observation device 91 is provided on the distal end of the overtube, positioning is easy. The size of the view field of the second observation device 91 can be readily adjusted by relatively changing the distance from the distal area of the overtube 90 to the target site W. Such an adjustment of distance can be achieved by the projected amount of the endoscope 1 from the overtube 90. In the present embodiment, similarly to the first and second embodiments, when a desired medical procedure is performed in the abdominal cavity AC, rotation and/or back-and-forth moving operation of the overtube 90 may be performed so as to change the position of the second observation device 91 to a desired condition (to change the viewpoint of the second observation device 91).

Fourth Embodiment

A fourth embodiment is described in detail with reference to the drawings. The present embodiment is characterized in that the distal end of an overtube is attached with a second observation device in a positionally adjustable manner.

Figure 18:
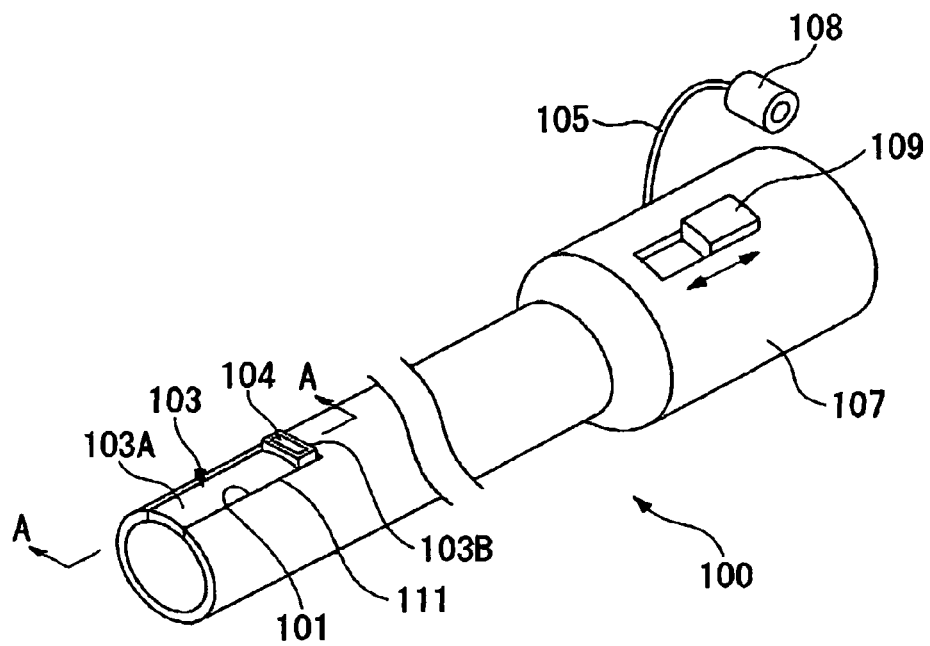
FIG. 18 is a view showing the second observation device provided on a rising member of the overtube.
Figure 19:
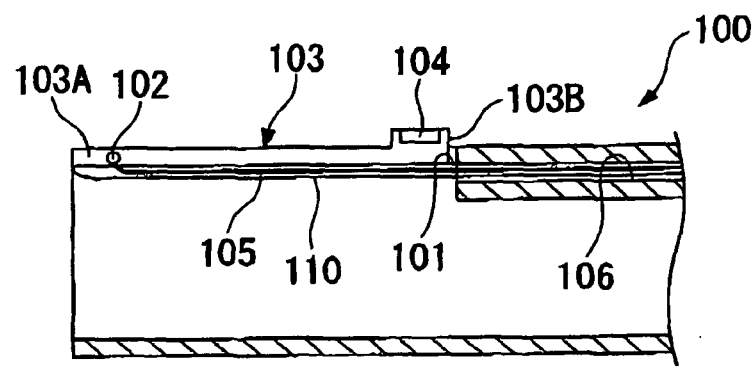
FIG. 19 is a cross-sectional view taken along the line A-A of FIG. 18.

As shown in FIG. 18 and FIG. 19, on the distal end of an overtube 100, an elongated slit 101 is formed along the lengthwise direction. The distal end side of the slit 101 is fixed with a pin 102 so as to transverse the slit 101. This pin 102 is attached with a proximal end 103A of a rising member 103. The rising member 103 has a shape to fit in the slit 101, and in a condition where it is accommodated in the slit 101, the outline of the overtube 100 is hardly changed. The distal end 103B of the rising member 103 is provided with a second observation device 104 oriented radially outward. An electric signal output from the second observation device 104 is output to a cable 105. The cable 105 is led out from the vicinity of the pin 102, and led out through a lumen 106 on the inner peripheral side of the overtube 100, to a proximal end 107 on the hand side. The cable 105 is led out from the proximal end 107, and the construction is such that an image can be obtained by connecting a connector 108 to the controller 24 (refer to FIG. 1). Furthermore, the proximal end 107 is provided with a slide member 109. The slide member 109 is slidable in the lengthwise direction of the overtube 100, and a wire 110 is fixed inside thereof. The wire 110 is guided through the lumen 106 of the overtube 100 to the distal end, and fixed to a distal side further from the pin 102 on the proximal end 103A of the rising member 103. The wire 110 has a flexibility but a predetermined rigidity, and is capable of raising the rising member 103 and pulling it into the slit 101, by moving the wire 110 back-and-forth.

Figure 20:
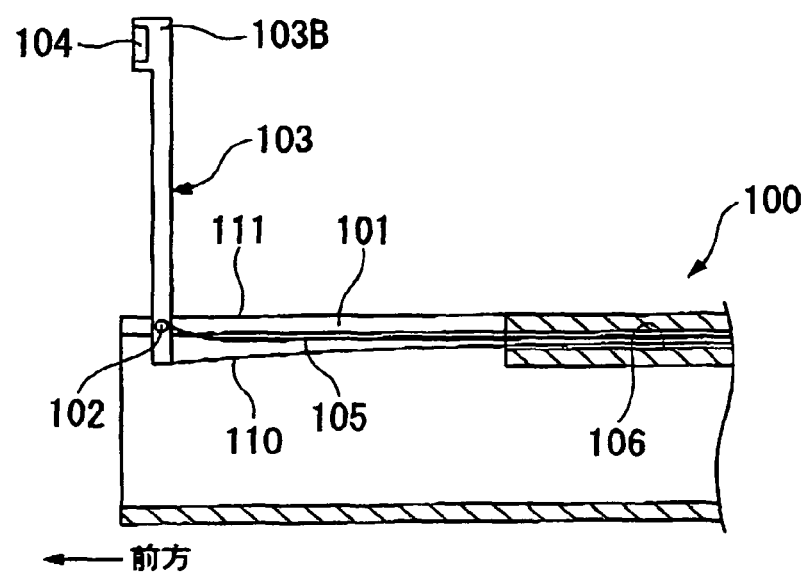
FIG. 20 illustrates the rising member raised from the position of FIG. 19.

When a manipulation is performed, the overtube 100 and the endoscope 1 are guided through the opening SO formed in the stomach ST, into the abdominal cavity AC. After the overtube 100 and the endoscope 1 are guided into the abdominal cavity AC so that the distal end of the overtube 100 reaches a desired position, the operator moves the slide member 109 backward. The wire 110 pulls the proximal end 103A of the rising member 103, to rotate the rising member 103 about the pin 102. As shown in FIG. 20, the rising member 103 rises so as to separate the second observation device 104 from the side face 111 of the overtube 110, and stops in a position approximately orthogonal to the lengthwise direction of the overtube 100. The second observation device 104 is arranged in a position away from the side face 111 of the overtube 100, and its observation view field direction is oriented forward in the insertion direction of the overtube 100 into the body. In this manner, by changing the position of the second observation device 104, an image obtained by the second observation device 104 becomes similar to an image in a condition where the target site W and the treatment tool are overlooked from the rear. The operator performs the manipulation while confirming two images having different image-capturing positions.

In the present embodiment, since the procedure can be performed using two images captured from different points in the insertion direction of the endoscope 1, the positional relation between the target site W and the treatment tool are readily confirmed, facilitating the procedure. Since the second observation device 104 can be arranged in the position away from the overtube 100, an image can be obtained from a different angle and a different distance from those of an image of the first observation device 6, facilitating the confirmation of position of the treatment tool and the like. The image of the second observation device 104 becomes an image as if the target site W of the patient PT lying on his back is overlooked. Therefore the operator can readily and sensuously specify the positional relation. The range of the second observation image obtained by the second observation device 104 can be readily adjusted by relatively moving the position of the distal area of the overtube 100 with respect to the endoscope 1 and the target site W. The second observation device 104 can be pulled in to fit the outline of the overtube 100, when it is not used. Therefore the insertion/withdrawal can be smoothly performed without enlarging the outer diameter of the overtube 100.

In the present embodiment, similarly to the abovementioned embodiments, when a desired medical procedure is performed in the abdominal cavity AC, rotation and/or back-and-forth moving operation of the overtube 100 may be performed so as to change the position of the second observation device 104 to a desired condition (to change the viewpoint of the second observation device 104).

Although the present invention has been described with respect to its preferred embodiments, the present invention is not limited to the embodiments described above. The configuration of the present invention allows for addition, omission, substitution and further replacement without departing from the spirit and scope of the present invention. The present invention is not limited by the above descriptions but is limited only by the appended claims.

For example, the arrangement may be such that only an image of the second observation device is used when the insertion portion 3 is faced to the target site W, and only an image of the first observation device 6 is used when an actual procedure is performed.

If the endoscope 1 has a plurality of work channels 10, manipulation can be performed using a plurality of treatment tools at the same time, improving the treatment properties.

When the endoscope 1 is inserted into the abdominal cavity AC, the arrangement may be such that the endoscope 1 is inserted from a natural orifice of the living body into another hollow organ, not limiting to the stomach ST, and then an opening is formed in the wall of the hollow organ, so as to introduce the endoscope into the abdominal cavity AC.

In the first embodiment, when the capsule endoscope 40 is introduced into the abdominal cavity AC, the arrangement may be such that an exclusive introducing device is used, and after the capsule endoscope 40 is arranged, the exclusive introducing device is withdrawn from the body, and the endoscope 1 is inserted instead. In the introducing device in this case it is sufficient to have a construction without the first observation device 6. Moreover, the introducing device may have a construction where a holding part is fixed to the distal end, without having the work channel 10 capable of exchanging treatment tools.

The manipulation may be performed by selectively displaying only one out of two images. For example, only an image of the second observation device is used when the location is confirmed, and only an image of the first observation device is used during a manipulation.

The hollow organ formed with the orifice SO is not limited to the stomach ST. For example, it may be an esophagus, a duodenum, a small intestine, a large intestine, a uterus, a bladder, and the like.

The device needed for performing a desired manipulation is not limited to the endoscope comprising the observation device and the work channel described in the above embodiments. For example, there may be used a device (hereunder, called a treatment device for convenience) comprising a treatment portion for performing a desired treatment, on the distal side of the insertion portion to be inserted into the body, and provided with an operation portion capable of operating this treatment portion from outside of the body. If the treatment device is provided with an observation device, an image from the observation device may be used as a first observation image. Moreover, if the treatment device does not have an observation device, various modes may be considered such as using the abovementioned capsule endoscope in common. Furthermore, as another example of the abovementioned treatment device, there may be used a device comprising a lumen through which the treatment tool can be inserted, in the insertion portion, but not having an observation mechanism.

Fifth Embodiment

Figure 21:
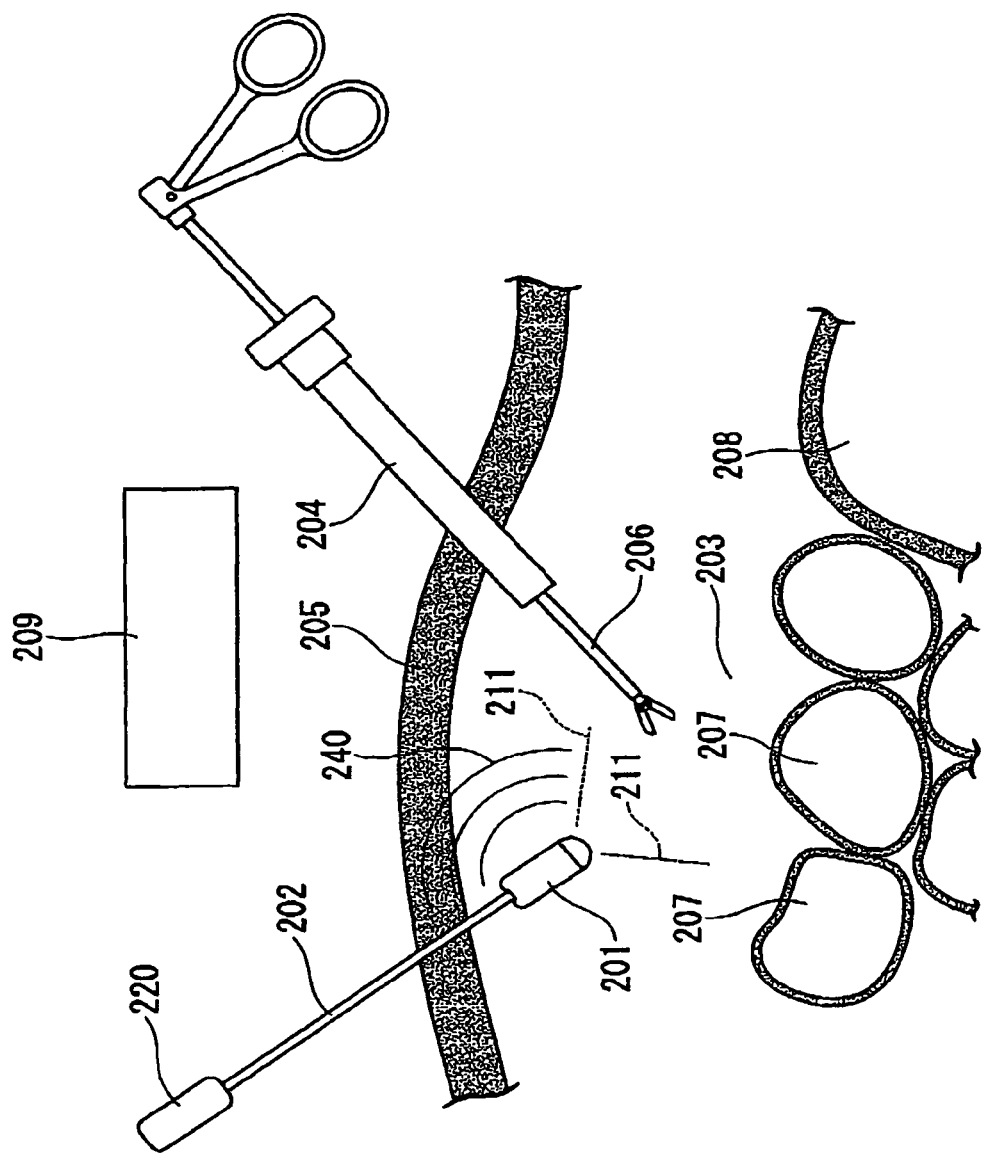
FIG. 21 is a schematic cross-sectional view of the human abdominal wall with an imaging capsule attached to the distal tip of a percutaneous manipulator placed through the abdominal wall. This capsule observes the action of a laparoscopic surgical instrument also placed through the abdominal wall, and sends the resulting images to an externally placed receiver via radio frequency transmission.

FIG. 21 provides an overview of the use of this new method of imaging the inside of the lumen of the abdominal cavity. The imaging capsule 201 is mounted via an easily attachable/detachable connecting means to the distal end of a percutaneous manipulator 202. The imaging capsule is used to observe the inside of the lumen of the abdominal cavity 203 and to guide surgery or therapy within the lumen of the abdominal cavity. Images created by the imaging capsule are sent by radio transmission 240 to a receiver 209 located next to the patient. One or more trocars 204 inserted through the patient's abdominal wall allow the introduction of laparoscopic surgical instruments 206 into the lumen of the abdominal cavity 203. The surgical instruments are used to manipulate, cut, burn, suture or perform other therapeutic activity on organs accessible within the lumen of the abdominal cavity. Such organs include gastrointestinal organs such as the intestines 207 and stomach 208, organs of the pancreatic and biliary systems, reproductive organs, etc.

It is well known that smaller stab incisions in the abdominal wall facilitate quick healing and reduce post-procedure pain and discomfort. Traditional laparoscopes range from 3 mm to 10 mm in shaft diameter. Typically laparoscopes with 5 to 10 mm shaft diameters are used because they provide a superior image compared to thinner instruments. However, physicians would prefer to use the smallest puncture possible, if image quality could be maintained. It is possible to maintain image quality with a high resolution imaging capsule mounted on a very thin percutaneous manipulator. The large diameter of the capsule allows it to contain a high resolution imaging system, while the very thin shaft of the percutaneous manipulator allows the capsule to be oriented and held in the abdominal cavity such that the field of view of the capsule is directed at the area of interest. The position of such a percutaneous manipulator can be controlled externally by the operator by grasping the handle 220 of the manipulator. Reference numeral 211 indicates a field view angle of the imaging capsule.

The advantages of such a system is that the percutaneous manipulator makes a very small puncture in the abdominal wall (e.g., 1 to 3 mm) and thereby introduces minimal trauma to abdominal wall tissue, speeding healing and reducing post-procedural pain. Furthermore, both the capsule and the introducer can be disposable, eliminating the need to reprocess these devices.

Figure 22:
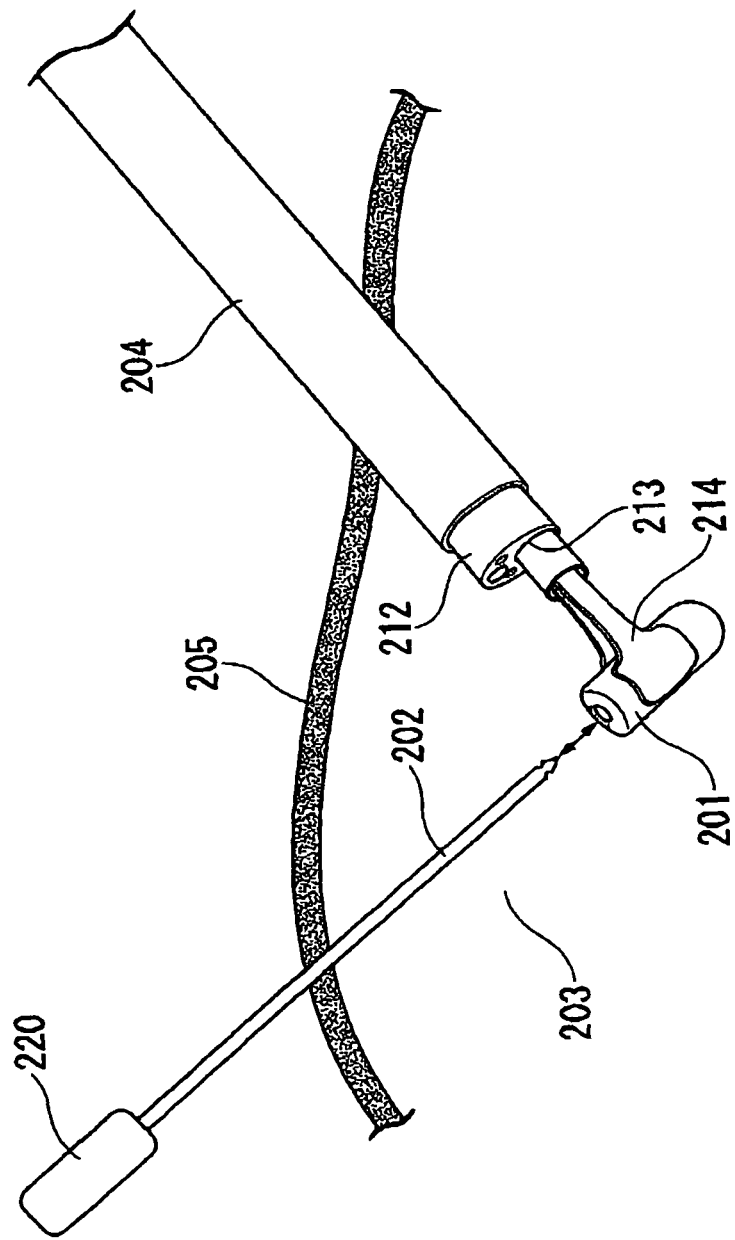
FIG. 22 is a cross-sectional schematic view of the abdominal wall illustrating an imaging capsule held by a laparoscopic grasping device in appropriate position for attachment to the distal tip of the percutaneous manipulator.

Prior to use, the imaging capsule must be introduced into the lumen of the abdominal cavity 203. One means of doing this is to put the capsule into the lumen of the abdominal cavity via a large trocar 204. After placing the capsule into the lumen of the abdominal cavity through the trocar, a laparoscope 212 with a therapeutic channel 213 and a grasping device 214 is used to hold the imaging capsule 201 and connect it to the distal tip of the percutaneous manipulator 202. This operation is illustrated in FIG. 22.

Figure 23:
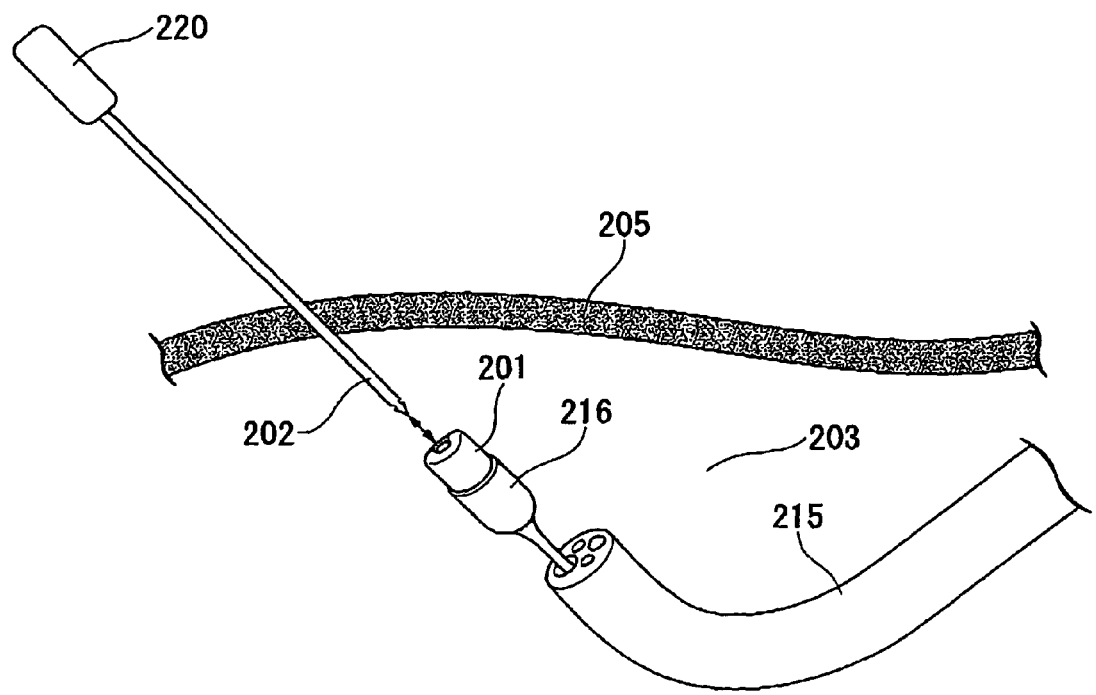
FIG. 23 is a cross-sectional schematic view of the abdominal wall illustrating a flexible endoscope holding an imaging capsule in a capsule holder in position for attachment to the distal tip of the percutaneous manipulator.

Alternatively, as illustrated in FIG. 23, the video capsule may be brought into the lumen of the abdominal cavity 3 by means of a flexible endoscope 215 which has entered the peritoneal cavity by means of an opening in the abdominal wall, the gastric wall, the intestinal wall, or other means of access to the lumen of the abdominal cavity. A holder 216 holds the imaging capsule 201 via suction, a friction fit, or other suitable means until it is attached to the end of the percutaneous manipulator 202.

Figure 24:
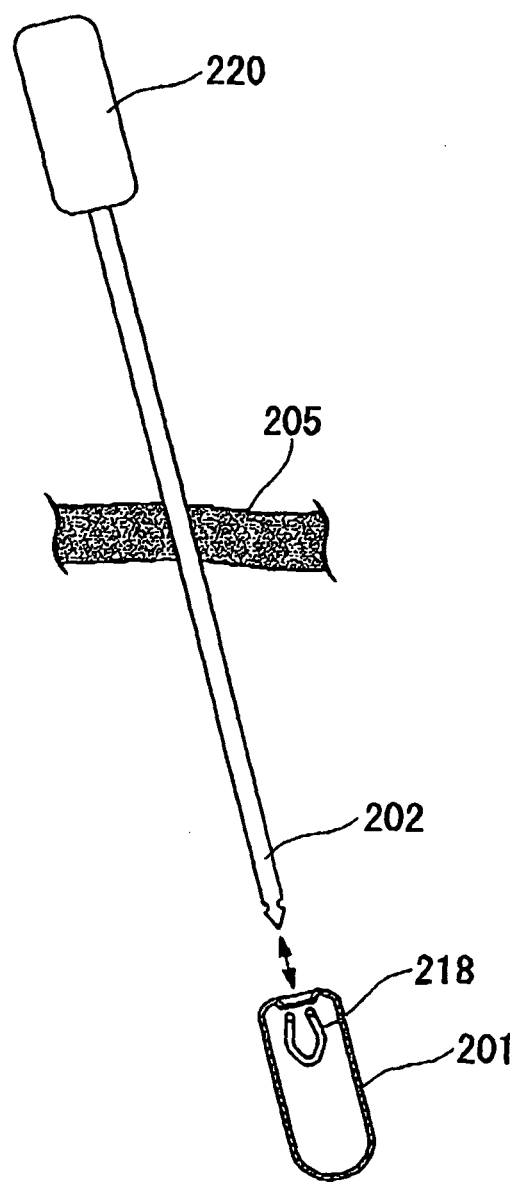
FIG. 24 is a cross-sectional schematic view of an embodiment of the imaging capsule illustrating how the imaging capsule is attached to the distal tip of the percutaneous manipulator by means of a spring clip.

FIG. 24 illustrates that to reduce the overall size of the puncture in the abdominal wall 205, the percutaneous manipulator 202 can be placed through the tissue directly. Alternatively, as FIG. 25 illustrates, the percutaneous manipulator 202 could be introduced through the abdominal wall 205 through a trocar 217 of appropriate size.

Figure 25:
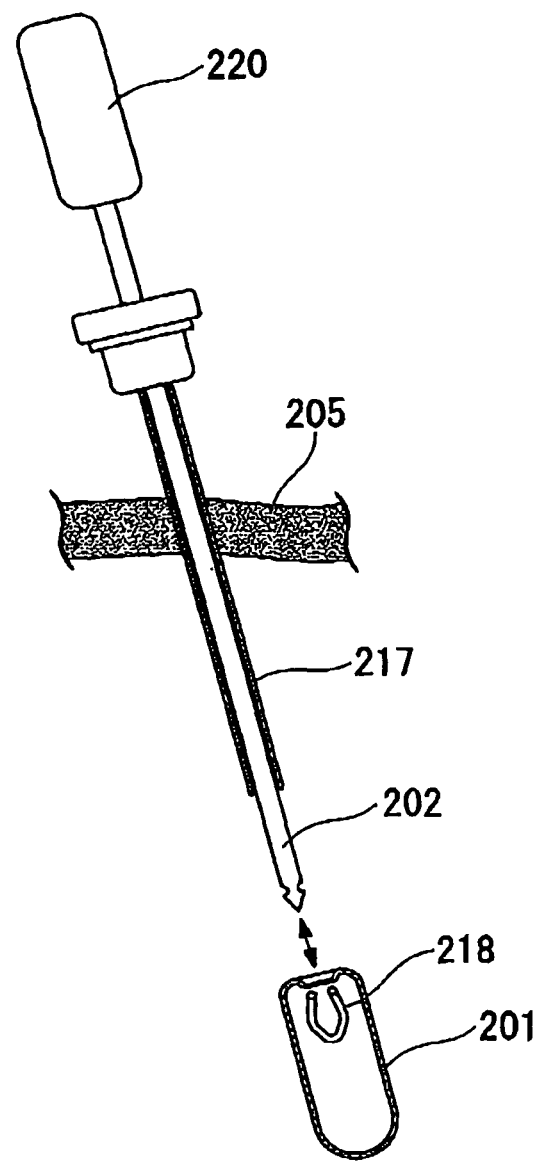
FIG. 25 is a cross-sectional schematic view of the devices of FIG. 24 illustrating that the percutaneous manipulator can alternatively be inserted through a trocar placed in the abdominal wall.
Figure 26:
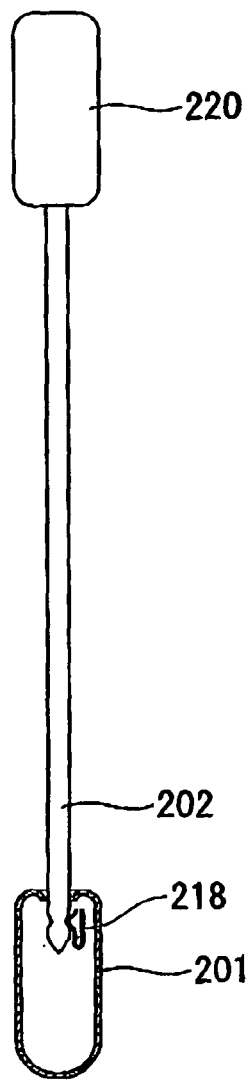
FIG. 26 is a cross-sectional schematic view of an alternative design for the spring clip holding the imaging capsule to the distal tip of the percutaneous manipulator.
Figure 27:
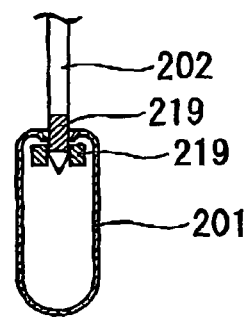
FIG. 27 is a cross-sectional schematic view of an alternative design for a means of holding the imaging capsule to the distal tip of the percutaneous manipulator employing magnets.

As FIG. 25 and FIG. 26 illustrate, the video capsule can be held on the distal tip of the percutaneous manipulator via various types of spring clips 218. Alternatively other means of easy attachment/detachment can be employed, such as magnets 219, as illustrated in FIG. 27.

Figure 28:
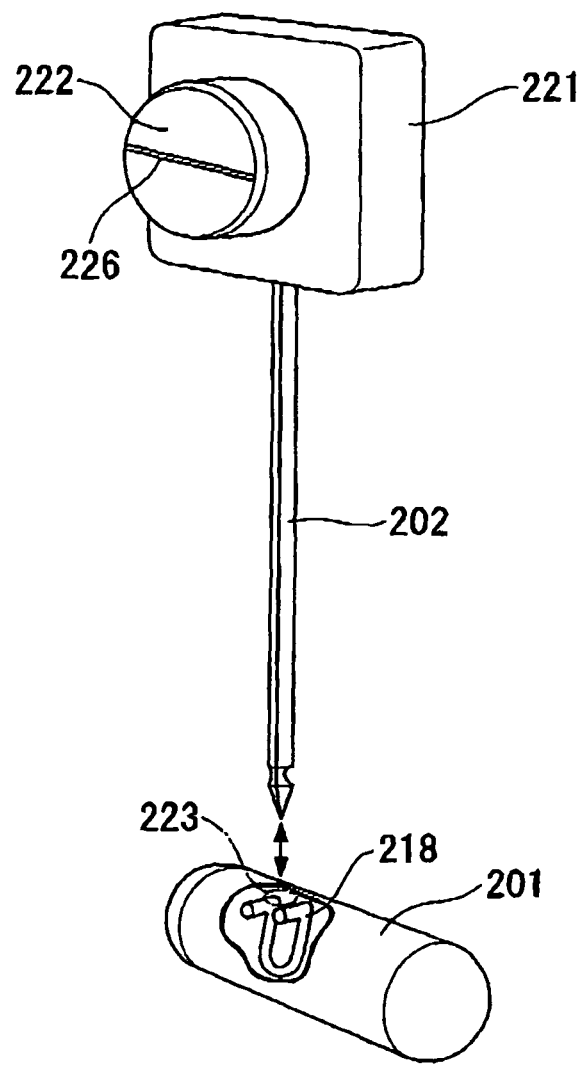
FIG. 28 is a schematic view of an alternative embodiment of a percutaneous manipulator with a control knob on the handle of the manipulator for changing the orientation of the imaging capsule attached to its distal tip.

While in many situations, manipulation of the percutaneous manipulator via its external handle 220 will be sufficient, this will require a constant grasp of the handle by the operator. Also, depending on the desired direction of view, it may be required that the shaft of the percutaneous manipulator be placed in a very awkward acute angle with the abdominal wall. FIG. 28 illustrates an alternative embodiment of the percutaneous manipulator 202 that has a handle 221 with a control knob 222 to change the orientation of the imaging capsule 201 which is connected to the tip of the manipulator. In this embodiment of the imaging capsule, the opening 223 for the connector is on the side wall of the capsule, instead of the end wall of the capsule. The capsule is attached to the distal tip of the manipulator via a spring clip 223.

Figure 29:
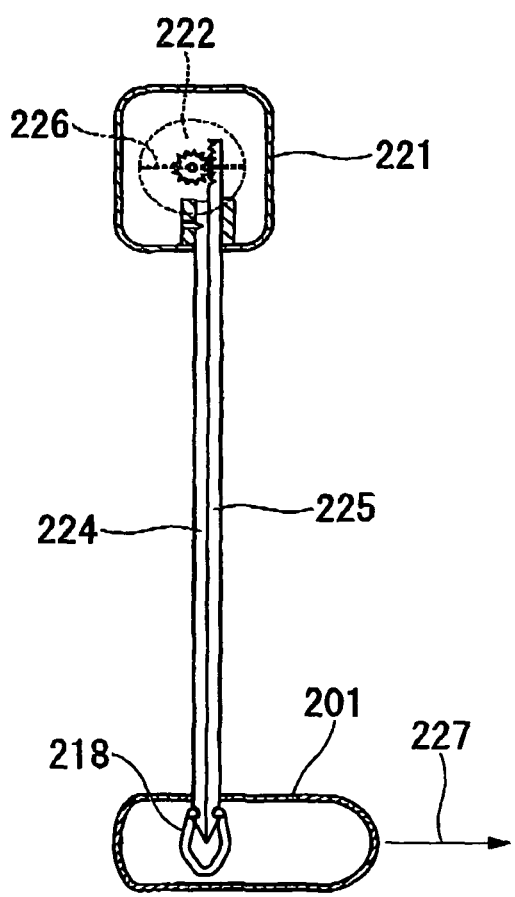
FIG. 29 is a side-sectional view of the embodiment illustrated in FIG. 28 illustrating a mechanism by which the control knob changes the orientation of the imaging capsule.
Figure 30:
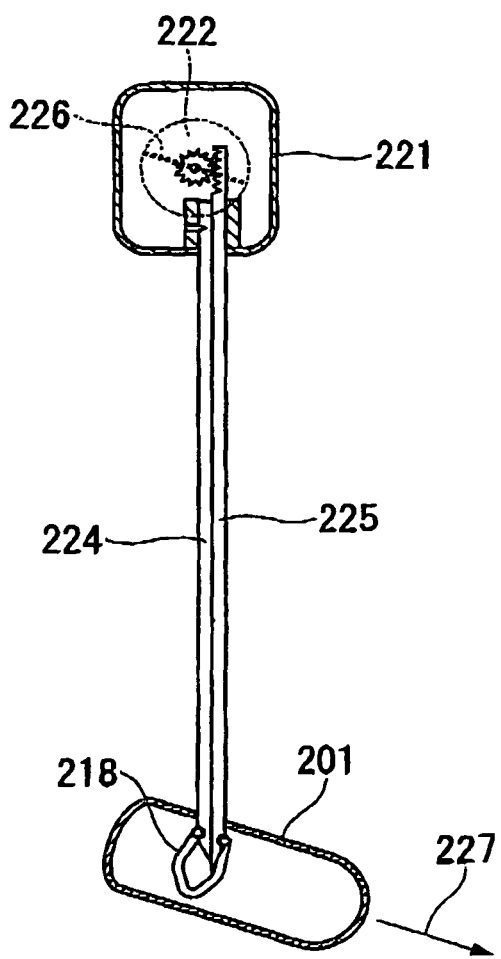
FIG. 30 is a side-sectional view of the embodiment illustrated in FIG. 29 illustrating that rotation of the control knob changes the orientation of the imaging capsule at its distal tip by means of changing the position of the shaft parts relative to the manipulator.

FIG. 29 illustrates one embodiment of a mechanism for controlling the position at which the capsule is held. The manipulator shaft is constructed of two parts 224 and 225 that connect to the imaging capsule via a spring clip 218. The relative position of shaft parts 224 and 225 is controlled by a control knob 222 on the handle 221. As FIG. 30 illustrates, rotating the control knob changes the relative position of the shaft parts 224 and 225 changing the orientation of the imaging capsule 1. In this embodiment, an indication mark 226 on the control knob shows the change in position of the capsule's direction of view 227. The capsule's direction of view 227 of the indication mark 226 is compared between FIGS. 29 and 30.

Figure 31:
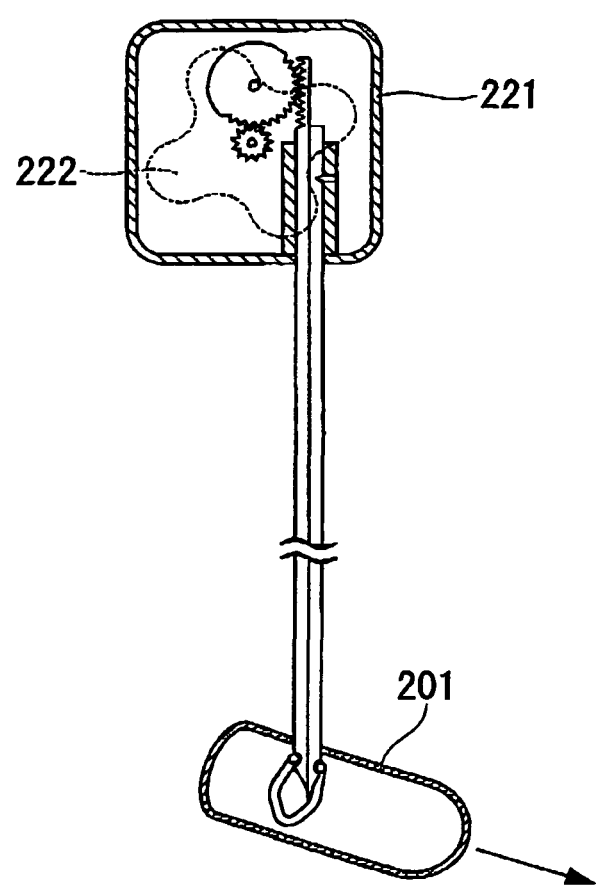
FIG. 31 is a side-sectional view of an alternative embodiment of the control knob and mechanism for orienting the imaging capsule attached to the distal tip of the manipulator.

FIG. 31 illustrates that various configurations of the gearing in the handle 221 of the percutaneous manipulator may be employed in order to change the sensitivity of the imaging capsule's orientation with respect to changes in position of the control knob 222.

Figure 32:
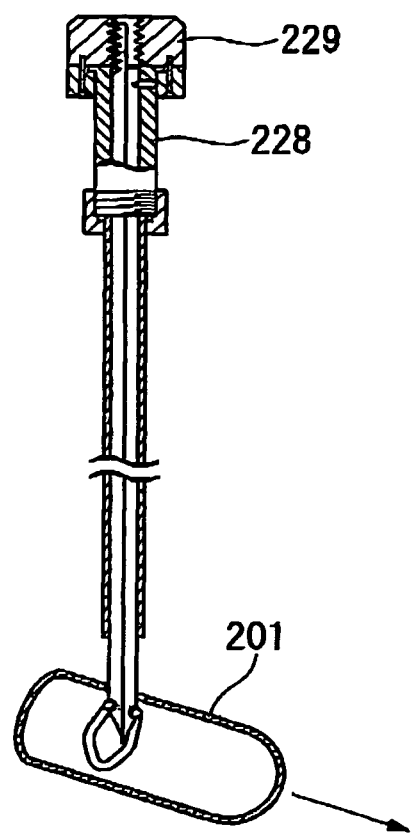
FIG. 32 is a side-sectional view of an alternative embodiment of the handle and mechanism of the percutaneous manipulator.

FIG. 32 illustrates an alternative embodiment of the percutaneous manipulator's handle 228. In this embodiment, rotating the adjustment nut 229 at the proximal end of the manipulator, changes the orientation of the imaging capsule 201 at its tip.

Figure 33:
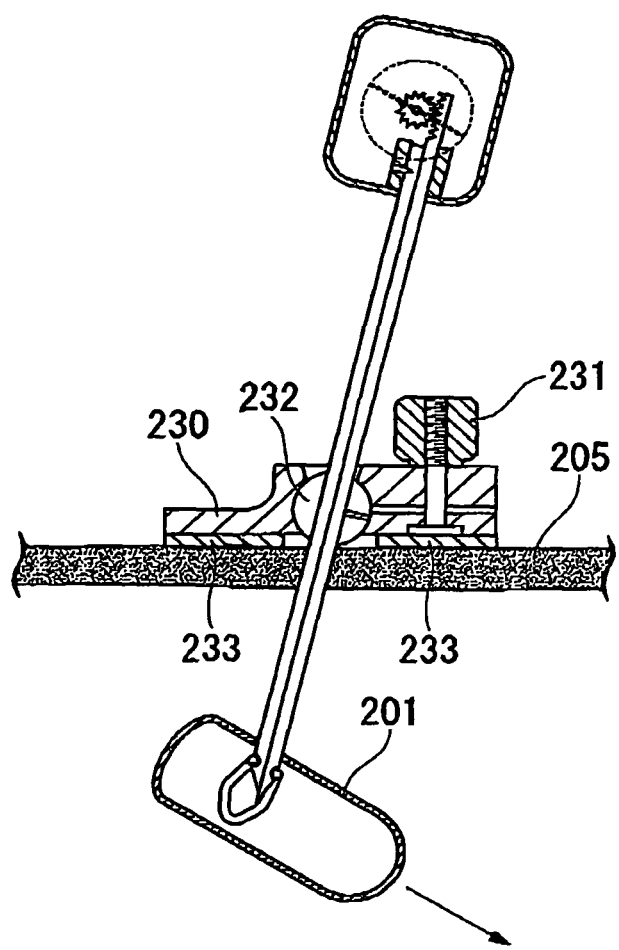
FIG. 33 is a side-sectional view of an attachment device that adheres to the exterior surface of the abdominal wall for fixing the position of the percutaneous manipulator.

FIG. 33 illustrates another embodiment of the invention wherein the percutaneous manipulator is held in position with respect to abdominal wall via an attachment device 230. The attachment device has a locking nut 231 that compresses a pivot ball 232 to lock the shaft of the percutaneous manipulator at the correct height and correct angle with respect to the abdominal wall 205. The attachment device 230 is held to the abdominal wall 205 by means of double-sided adhesive tape 233 placed between the attachment device 230 and the patient's skin overlying the abdominal wall.

Figure 34:
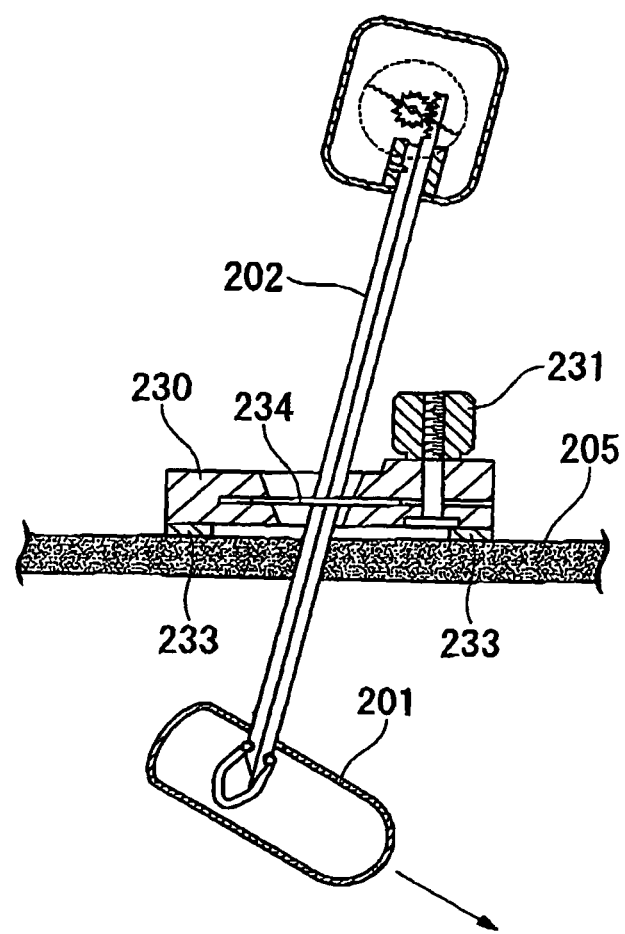
FIG. 34 is a side-sectional view of an alternative embodiment of an attachment device that adheres to the exterior surface of the abdominal wall for fixing the position of the percutaneous manipulator.

FIG. 34 illustrates another embodiment of the attachment device. The shaft of the percutaneous manipulator 202 passes through a rubber membrane 234 that slides in a slot in the attachment device. When the percutaneous manipulator is in the correct position, the locking nut 231 is tightened to hold the manipulator in position with respect to the abdominal wall 205.

Figure 35:
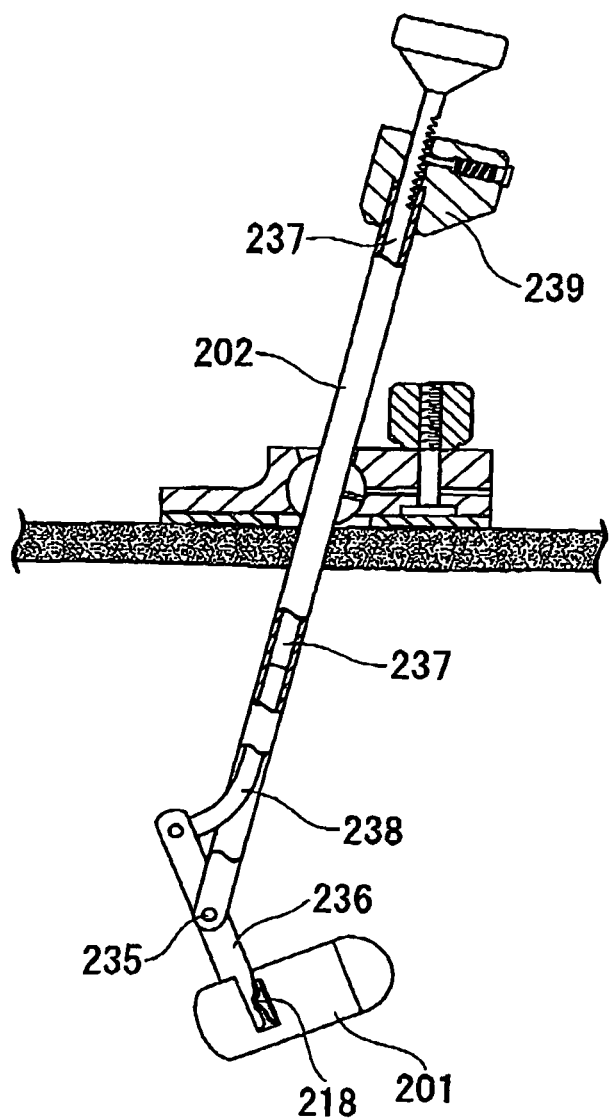
FIG. 35 is a side-sectional view of an alternative embodiment of the percutaneous manipulator. A ratchet on the proximal end of the manipulator controls the position of the attachment arm to which the imaging capsule is attached. An attachment device fixes the position of the percutaneous manipulator with respect to the abdominal wall.

FIG. 35 illustrates another embodiment of the present invention. In this embodiment, the distal end of the percutaneous manipulator 202 has a hinge 235 allowing movement of an attachment arm 236 that connects to the imaging capsule 201 by means of a spring clip 218. The position of the attachment arm 236 is controlled by a rod 37 in the percutaneous manipulator. The rod 237 is connected to the attachment arm 236 by means of a flexible member 238. The flexible member is joined to the rod 237 whereby movement of the rod causes the attachment arm to rotate about the hinge 235. A ratchet 239 at the proximal end of the device allows the position of the rod 237 to be changed easily, yet holds the rod in the selected position.

Many other embodiments of the percutaneous manipulator, the means of connecting the capsule to the manipulator and the means of mounting the manipulator to the abdominal wall will be apparent to users of this invention. The objective of the invention is to control the direction of view of an imaging capsule placed in the intraperitoneal space via a manipulator that is passed through a small puncture of the abdominal wall. The advantage of this invention over a standard laparoscope is found in the relatively small diameter of the manipulator shaft compared to the relatively large diameter of the imaging capsule. The compact manipulator shaft can be inserted through the abdominal wall by means of a very small stab incision that will heal quickly with reduced post-procedure pain. Yet the imaging capsule is of a sufficient size to produce high resolution images of intraperitoneal tissue.

What is claimed is:

1. A medical operation comprising:
   introducing a holding member having a first holding portion which is provided at a distal end of an insertion portion into an abdominal cavity through an opening which opens percutaneously;
   introducing an introducing device having a second holding portion which detachably holds an observational device having a connecting member which is detachably connected to said first holding portion into the abdominal cavity through a natural orifice;
   fixing said first holding portion to said connecting member of said observational device;
   detaching said second holding portion from said first holding portion which is fixed to said observational device and to said connecting member after fixing said first holding portion to said connecting member; and
   observing said abdominal cavity by controlling a position and direction of said observational device that is fixed to said first holding portion by operating said holding member, in the state where said observational device is separated from said second holding portion.

2. The medical operation according to claim 1, wherein the introducing of the introducing device comprises introducing a laparoscope into the abdominal cavity, and said second holding portion is a grasping device which grasps said observational device.

3. The medical operation according to claim 1, wherein the introducing of the introducing device comprises introducing a flexible endoscope into the abdominal cavity through a natural orifice, and said first holding portion is a manipulator which holds said observational device.

4. The medical operation according to claim 1, wherein said observational device is a capsule endoscope.

5. The medical operation according to claim 4, wherein the connecting of said first holding portion and said observational device comprises connecting said first holding portion and said observational device in a direction which is perpendicular to an observation direction of said capsule endoscope.

* * * * *